United States Patent
Kaeppler et al.

(10) Patent No.: US 10,440,911 B2
(45) Date of Patent: Oct. 15, 2019

(54) TARGETED MODIFICATION OF MAIZE ROOTS TO ENHANCE ABIOTIC STRESS TOLERANCE

(71) Applicants: Wisconsin Alumni Research Foundation, Madison, WI (US); The Penn State Research Foundation, University Park, PA (US); The University of Nottingham, East Midlands (GB)

(72) Inventors: Shawn Michael Kaeppler, Oregon, WI (US); Patompong Saengwilai, Bangkok (TH); Jonathan Paul Lynch, Boalsburg, PA (US); Malcolm John Bennett, Nottingham (GB); James Johnson, Whitestown, IN (US)

(73) Assignees: Wisconsin Alumni Research Foundation, Madison, WI (US); The Penn State Research Foundation, University Park, PA (US)

( * ) Notice: Subject to any disclaimer, the term of this patent is extended or adjusted under 35 U.S.C. 154(b) by 0 days.

(21) Appl. No.: 15/704,502

(22) Filed: Sep. 14, 2017

(65) Prior Publication Data
US 2018/0077892 A1 Mar. 22, 2018

Related U.S. Application Data

(60) Provisional application No. 62/395,434, filed on Sep. 16, 2016.

(51) Int. Cl.
| | |
|---|---|
| *C12N 15/82* | (2006.01) |
| *A01H 5/10* | (2018.01) |
| *A01H 1/06* | (2006.01) |
| *C07K 14/415* | (2006.01) |
| *A01H 6/46* | (2018.01) |

(52) U.S. Cl.
CPC .......... *A01H 5/10* (2013.01); *A01H 1/06* (2013.01); *A01H 6/4684* (2018.05); *C07K 14/415* (2013.01); *C12N 15/82* (2013.01); *C12N 15/8242* (2013.01); *C12N 15/8271* (2013.01)

(58) Field of Classification Search
None
See application file for complete search history.

(56) References Cited

U.S. PATENT DOCUMENTS 4,683,195 A 7/1987 Mullis et al.

OTHER PUBLICATIONS

Maize Genetics and Genomics Database, UniformMu Transposon Resource, Mar. 2011 (Year: 2011).*

Bates, D., Maechler, M., Bolker, B., and Walker, S. Fitting linear mixed-effects models using lme4. Journal of Statistical Software. 67(1):1-48 (2014).
Burton, A. L., Williams, M., Lynch, J. P. & Brown, K. M. RootScan: Software for high-throughput analysis of root anatomical traits. Plant Soil 357, 189-203 (2012).
Burton, A. L. et al. QTL mapping and phenotypic variation of root anatomical traits in maize (*Zea mays* L.). Theor. Appl. Genet. 128, 93-106 (2015).
Chimungu, J. G., Brown, K. M. & Lynch, J. P. Reduced root cortical cell file number improves drought tolerance in maize. Plant Physiol. 166, 1943-1955 (2014).
Chimungu, J. G., Brown, K. M. & Lynch, J. P. Large root cortical cell size improves drought tolerance in maize. Plant Physiol. 166, 2166-2178 (2014).
Chimungu, J. G. et al. Utility of root cortical aerenchyma under water limited conditions in tropical maize (*Zea mays* L). Field Crops Res 171, 86-98 (2015).
Dellaporta, S. L., et al. Molecular Cloning of the Maize R-nj allele by transposon tagging with Ac, Chromosome structure and function, (1988) p. 263-282.
Drew, M. C., He, C. J. & Morgan, P. W. Programmed cell death and aerenchyma formation in roots. Trends Plant Sci. 5, 123-127 (2000).
Gao, X., Starmer, J. & Martin, E. R. A multiple testing correction method for genetic association studies using correlated single nucleotide polymorphisms. Geneic Epidemiol. 32, 361-369 (2008).
Grassini, P., Eskridge, K. M. & Gassman, K. G. Distinguishing between yield advances and yield plateaus in historical crop production trends. Nat. Commun. 4, 2918 (2013).
Gunawardena, A. H. L. A. N. et al. Characterisation of programmed cell death during aerenchyma formation induced by ethylene or hypoxia in roots of maize (*Zea mays* L.). Planta 212, 205-214 (2001).
Hansey, C. N., Johnson, J. M., Sekhon, R. S., Kaeppler, S. M. & Leon, N. De. Genetic diversity of a maize association population with restricted phenology. Crop Sci. 51, 704-715 (2011).
Hirsch, C. N. et al. Insights into the maize pan-genome and pan-transcriptome. Plant Cell 26, 121-135 (2014).
Lipka, A. E. et al. GAPIT: genome association and prediction integrated tool. Bioinformatics 28, 2397-2399 (2012).
Lynch, J. P. Roots of the second green revolution. Aust. J. Bot. 55, 493-512 (2007).
Lynch, J. P. Root phenes that reduce the metabolic costs of soil exploration: opportunities for 21st century agriculture. Plant. Cell Environ. 1775-1784 (2014).

(Continued)

*Primary Examiner* — Eileen B O Hara
(74) *Attorney, Agent, or Firm* — Quarles & Brady LLP

(57) ABSTRACT

The present invention relates to crop breeding. More particularly, the present invention relates to targeted modification of root to enhance abiotic stress tolerance in maize. In one aspect, the invention provides recombinant maize exhibiting increased root cortical aerenchyma (RCA). Methods of making the recombinant maize and various methods of plant selection and breeding are further provided.

8 Claims, 9 Drawing Sheets
(4 of 9 Drawing Sheet(s) Filed in Color)
Specification includes a Sequence Listing.

(56) References Cited

OTHER PUBLICATIONS

Mano, Y. & Omori, F. Flooding tolerance in interspecific introgression lines containing chromosome segments from teosinte (*Zea nicaraguensis*) in maize (*Zea mays* subsp. *mays*). Ann. Bot. 112, 1125-1139 (2013).

Mano, Y. et al. QTL mapping of root aerenchyma formation in seedlings of a maize × rare teosinte '*Zea nicaraguensis*' cross. Plant Soil 295, 103-113 (2007).

Niu, N. et al. EAT1 promotes tapetal cell death by regulating aspartic proteases during male reproductive development in rice. Nat. Commun. 4, 1445 (2013).

Postma, J. A. & Lynch, J. P. Root cortical aerenchyma enhances growth of *Zea mays* L on soils with suboptimal availability of nitrogen, phosphorus and potassium. Plant Physiol. 156, 1190-1201 (2011).

Rajhi, I. et al. Identification of genes expressed in maize root cortical cells during lysigenous aerenchyma formation using laser microdissection and microarray analyses. New Phytol. 190, 351-368 (2011).

Richards & Passioura. A breeding program to reduce the diameter of the major xylem vessel in the seminal roots of wheat and its effect on grain yield in rain-fed environments. Aust. J. Agric. Res. 40, 943-950 (1989).

Saengwilai, P., Nord, E., Chimungu, J., Brown, K. & Lynch, J. Root cortical aerenchyma enhances nitrogen acquisition from low nitrogen soils in maize (*Zea mays* L.). Plant Physiol. 166, 726-735 (2014).

Sekhon, R. S. et al. Genome-wide atlas of transcription during maize development. Plant J. 66, 553-563 (2011).

Stelpflug, S. C. et al. An expanded maize gene expression atlas based on RNA-sequencing and its use to explore root development. Plant Genome (2015). doi:10.3835.

Subbaiah, C. C. & Sachs, M. M. Molecular and cellular adaptations of maize to flooding stress. Ann. Bot. 90, 119-127 (2003).

Sutton, M. A. et al. Too much of a good thing. Nature 472, 159-161 (2011).

Takahashi, H., Yamauchi, T., Rajhi, I., Nishizawa, N. K. & Nakazono, M. Transcript profiles in cortical cells of maize primary root during ethylene-induced lysigenous aerenchyma formation under aerobic conditions. Ann. Bot. 115, 879-894 (2015).

Trachsel, S., Kaeppler, S. M., Brown, K. M. & Lynch, J. P. Shovelomics: high throughput phenotyping of maize (*Zea mays* L.) root architecture in the field. Plant Soil 314, 75-87 (2011).

\* cited by examiner

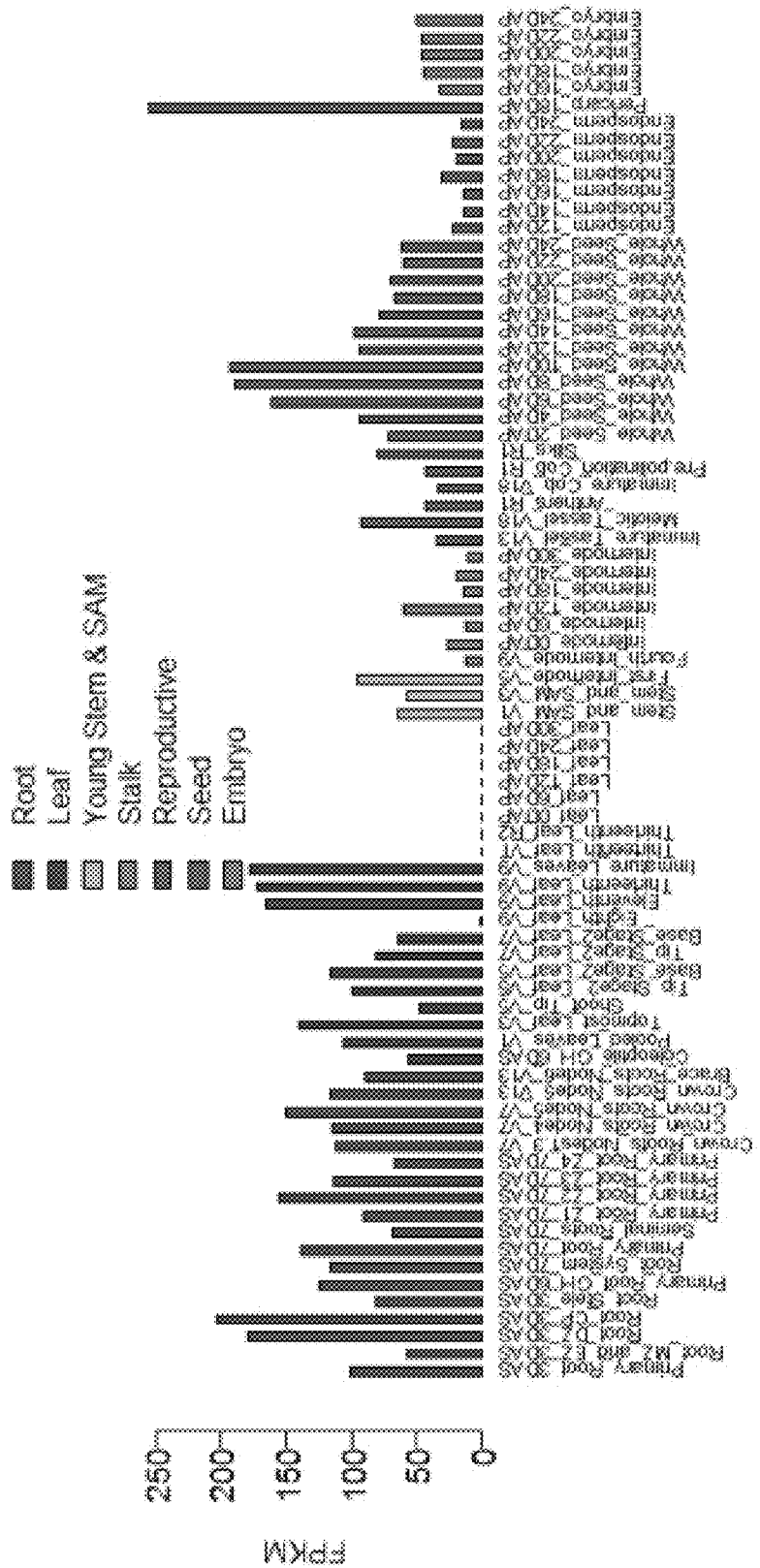

FIG. 4

Genomic DNA sequence corresponding to Zm0001d006065

```
>lcl|Zm0001d006065 Zm0001d006065   (SEQ ID NO:1)
GCAGCAAAGCAAGCTAAAGGAGAGAAACCTCATATACTTGCACTTTCGTCATAATCGTAAGATCAGAAAAAAATGCAAC
AAACATGACACGGTATCGTTCCAGTACCAGCCACCAGCGGTCTTACATAGGAGTAATAATCAGTACAGCTTCAGATGATG
GCGCATGTAATATTTGCGCCATATCTACCTAGCACACGACCTACTCCAATTTTTCACGAGATGGGTCGCACGATCTCTAT
GGGGGGCAAGAATCGAGTCGCCATGTGACATACGTGCAGCAGTATCACGGAATGAATTTCAGCTCGCAGTCGCAGTCGCA
GGCCTAAACGCTAATGATGGTCAGCTTAGCAGAGGAGAGCTCTGCTTGAAACACACAGCCCACACACAGGTCTTGGTACC
ACCACCACCTATGTACAAAAATACCAGCCCTTGCAGATCACCAGGGACGGGCTAGAACTCAGCCTTCGCCTGATCAGCTT
GCAACTGGCTGCATCACATACATATACAGCAACACATGGTTGGGGTTATCAGTCAAATAATGGTAATCTCCCGAATGGTG
CCCGCTTCAATTGATCGTCCATCACTCACATACCATCAAAGGTCGGGTACTAAAAGCCCATCCTCCTCCTGCCTTTGCTC
GCTACCGGTAGTAGGGGTAGGCAAAGCATGCTGTAGGCCATCCTCCCACAAGTCCCTTTGCTGAGAAATATGCCAGAACT
GTTATAAGATCCATATTGACAGCCATTAACTAGCTATACAGATTGCTGATTCCTCGGGCAAACATTTCTACCTGCTTTTG
AAAAGCAAACTGTGGGCTGGCCGCGTGGGGCAGAGCCGTGTCTAGCAGCAGGCTAGAGAGCACTGATCCTCCATACCAC
TACCGCTACCGCTACCACCCGAGCCAAAGCTGTGGAAAAGATCCGCCTGCTCGCAGAATGGAAAAGCTGCGCCGGCGCTT
TCCAGTCGAAAGACCGAACTTGCCGAAGGGCCACCACATGGCTGTTGGTACATCTGAATTAACCAGGATAAAATAGGCGTG
TGTCAAGCCGCGGATTTGATGTGCAGGTACAGAGCATCGGAGATTGATGTGTGGGTCAAGCTCACGTCTTTGTGCAGGAGT
GTCGATAGGTTGCTGAAATCAAGCTCTGGGTTCACAGTGGCGAGCTTCATGGACAGGAACTGAATAAAAGTAGTGTTAAT
AAACAGCAAAGAAAAAAAAACGATTGGAATCTCGAGCTATGACTGTGTTATTATGTAACCAAATGTAAGTGGAACCCT
CGCCTCACCTCAACTTGCTGCTGCAGCGACTGGACGTAGTTTATGATCTCATCGAGCATGAGTGCCTTGCCGACCACCTA
CAGTAGGGAATCCCCGTCAAATTACAGGCAGCAATTGACACGTTACACACGGACAATTCACTGTCCAAGAACTCCATGGCCAT
ACCTTGTTGCATCCTGGCACTAGGTCCTGTAGAAATTTCATCCTCTGGCTAATCTTCTCTCTTCTAACCTATCAAGACAC
AAATAACAAAAGTGCGGTTGTGAATTCAAACCCGAAGCACAAAATTTCCATTTTGCGATTTAGCCCAAACGGTAGGTAGA
AATGGAATTGCAGTGTCTTACCCTCTCGCAAGGCTGTGGCTGTCAGTCGCCTGCCCCGCCGCGCCCGGACATGGACGT
AGTCTTTGGGCCGGTTCGACTGCCGGCTTCGAGCTCTTCCCCTTGCCCTTCTTCGCGCTTTGACTTCAACCAAGGCGTCG
CTCGCCGCCGCCTCCTCCTCCTCTTCCTTGGCTTCACCGGACTGTCGCTGGCACCCACTACTCTGCACCTCTTCCCGTC
CGGACCCTTGGCCTCCGCAACCTGCAAACCAATATCGAGAATGGCGGCCACCGGCACGTCAAGAACCAGCAAGCTAAATTC
AAAGCACAGTCCACTCGCGCACAGTCGTTTCGTTTCCGCACCTTGCTCAAGCAGGCCTCCTTGCCACCGGCGGACCCCGTG
GGCGGCGCCTTGCGTTTCCTGGCATTGCGGTAGTCCCTAGCGCGCGCCCACGCTGGGTCGGACACCGACGACCCCTCCGG
AGACCCCGCCGCCACACCCTGCCTTCGCGGGCACCCCGAAGAGGCCCCGCCGCCGCCGCCGTAGCGTGCGAGGAACC
CGGCGTCCAGCGCGGCGAAGCTGAGTGCAGGGGCGGATGAGCCCATGAGCAGGCTGGCAATGTAGTCGCTGTCCATTGAA
ACAAACAAAGGCGCTGCCGCAGGAATTGCCCAGGAAGCAAAGGGAGGGTGAGGAAGTCTTGGGTCGTCTCTCGTCTACTG
CGAGCTCGAGTCTGCAATGGATTTGGGGCAAAGCGAAGCGACCGAGGCCGCGGAACCGCTAGGTGGGGGATTGCTTTATA
GAGCGGTTGTTGCCGCTGCGGTTGGGGTTCTGGGCCGCGGCCGCATCCGTGCGGTAGCTCGGCGGGGTGCGATGCTTGCG
CCGGTGGGGTTACCACCGGGTTATACTGCCGCGGCGCTCGCGCAGGAGAGGGGAGAAAAGGCGGTCAAAACGGGACGGAGC
GGGCGGAGGT
```

Genomic sequence of region including Zm0001d006065 beginning 5kb downstream and continuing 5kb upstream of the gene model, so includes promoter and enhancer sequences in addition to other sequence.

```
>Chr2:197126272..197138841   (SEQ ID NO:5)
GAATGCTGATTGCTGTGTTGCAGCTCTTCCTGCTGAATTAGTTGCTCATCTAGCAAGGGG
GGTTGAGGGTCTTGCTGAGCGGCTGCTCATTCACAATCCACTGATCCCACTCTCCCTGC
CCCAAGTCGTCCTGCTGAGCCGGCAACACTCCACCCTCAGGCTCCGGAGGAAAGTTAAGG
TCGAGCCCAGCCGGGGCAAAGGTTGGCCCAGCCCGAAGAAGGCCAGGGGGAGCTGATGA
CCATCCTCAGGTGGCGGAGGGATGGGGTCCTCGTCCTGAGCCTGACCGCCAAGCATAAGC
TGCTGGATAAATTTCACATTGTACCGTCCAGGAATCCCCAGCAAAACCCTCAGCCTCCGAA
AAAACAATAAATTGAGGAACCTCCTCAAGCGAAGTGACCCGAACACGGAGCAGGGTTCTA
GAGATATTGCTTCGGTCCTCCTCCCACAGAATCAGCCTCCCGAATGCCCCAATGGCGGCC
TGCAGATACTCCGAAGAACGATAATCCAAGGGAAAGCCCAGAAGCATAAGCCAACATTCA
TGGTTGAAGAGAAGGGCACGGTGGTTCCAGGCATCATTGTGACGGACCGCGGTGAATGTA
GCGTCCAAATACTGCTGGGGACCAAGAAGAACCAAGTTATCCCGCTCCAGCACACTACGG
AATTGCACCAACACTTGTCCCAAATGTGAGCGCTGAATGGCACGGACACCAACCCTCTGA
TGCTCCACAAGGTATTCCCTGACCACATCCCTAACCGCAGGGAACAAGACCTCGTGCTCC
GGTAAAGGATGGATATTTATAATCGCCCAGTCCTCATGAAATGGCGGCAAACGCTGCGAA
ACTGACCTGACCATAATCCCACGATGTTGGACCACCGCGGCGCTGAATCCTGGAGGGAGG
```

FIG. 4 (continued)

```
AACGGCCCCGGGTCCACACGCCGGTACGCCATTGACAGATTCTCAGACGATCGCCGGAGA
GCAAAGGGTGGAGAAGCAGGTTGGGGTTTTGTTGAAGTGACACCCAACGCGAGCTCCAAG
GACGTCTCTGGCGCCTGTTCGGGTTTTTTTAATAATGAAACCGCTTTGGCGAATTCACCG
AAGGAGGCAAATGAAGGTGGAGTCCCACCCGTCAGAGACCTGGAGGATGAGCGGAACCAG
GACCCGAAGTCCAAGGGACGGAGTGACCCTTCCAAAGGGCAGATACTTTCGAAGGAAGGG
AACGAGGAGAGAGGGAAACCAAATTCTGATTTTTTACGTTTGCAGAACAATTCCAAATGC
CCCCTGGCTTTACAAAAAAGGCAGAACAAGGCTGAAGTAGCCGAGCCCGACAAATCCGTC
CTTCCAGGCCCAAGCACAGGCCTGAGGGGCCCGTTACGCAGAATGGGCCGCCACTGCAAC
CTACGAGGCCAATGTCGCCCAACAGAAGAATTTGAGATCGACTTTGAATTTGAAGGGAG
CAATCATCACAGCCCCGACAACCGCGCCCATTCCTGCACCCGTTAGGCCTGGGAGAACAC
GCCGCAGGGGCAGACTCACGATGAAGATCACGCGACGAGGCCCCGAGGTCGAAGAGTTG
GCAGGAGACCTCGGACCCCGAGCTCCGAAGGGGAAACCCAATCTATTGAAAACAGAAGTC
CTCGGAGCAATCAATTTTCCAGCTGAACAGGAAGAACGACGAAGTCGACGAACTGGAACA
GCATTTGCACCAGTCAAAGGCGGGCGCCTAACCACATCAGCGAATGAGATTTTTTCCTG
CCCGAGACAAACCACCAGTTGGCGTTCTCCTCCTGAAGAAATAGCTTGAGCTCATAGTTC
CAATTTGGTCCACCCGAGTTCCACAAGTTGAAGAAAGCTTTGAATTCAGAACGAGCGATG
CATCTGGAGTTGTAGATGTGGAACCCAACATCCCTGGAGGAAACCGAGAAACGGAAAACC
CGATCGGCAAGCGGGAGGACCATGAATCCCCTGGCAGAACCACCAAAAGCAGCTTGAAGG
ATGTGACCAATCGAGACAGGATCAAGCCTGAAGATGCATCTTCCAAACGAGACAACAAGC
CAGAAAGCCGATGGGGAGCGCGGGCTTCCGGGGCAAACAGGAGAGGAAAATCGGCGCCAA
ACATCAGCCTCAAAAAGCACCCCCGGCCGAAAGTCCAGACGAGACAAATCCATCCCCCAG
CACGAAGAAGACCAAGCGAGGAGAGGGGGAGAGAAGCGAGAACCACGGGTGCGAAGTCGA
CGAAGAAGAGGGGGACCAAGCTCAGAACCAACTCACAGGAGGAAGCCGCGTGCGCGCGGC
CGCCCGCCGAGCGCCCAGTTGGTCACCGCCCATCTCCGCCATTGGCAGCTCCATCTTTCCA
TCAACGGAGAATGGAGGAGGGGAAGAGCGGCGTCGCAACGCTGCGCGCGGAAACCGGCCTA
CACACCGAGGAGAGCCGGCGGCAGCGGGGCTGGGGAGAAGCGAGAACCACGGGTGCTCCT
TGTCTTCAGTTTGGTTGTATGTTATTATACTATCTCATGTTTTATGACCGGTGGAGCCAT
CTGTGTCTATGATTTGTAGACTCGGTGGCATACTAGCGAGACCCACAAATCATAATGGCA
AAATTGCCAATGTCTGGACATCCGACCCTGCCCAAACAGACAGTTTTGCTCGCAGCTAGG
AAGCCCTACTACAGCTGAACACGTCGATGTCACCGAATAGGACTGATGAAGACAGATGTT
AAATGGGAAACGGGCTGACTAGTTTATGCGAGTAGAGGTTTGCTAGTGAATGTATCCCAC
AAGCGTGAGGAACACGGGGTATATCAACCAGCTTGACAAACGACAACAACTGCAACAGTG
AAGTAATTATGTCATCCCACGGGTATCTTGTTTATGTTTCAGATGCTAGAGTTCATTTTA
ATTTTGTCTTAGGAGATCACACTTTTTTCTAGTTTAGGCTAAATTTACTATTTAAATCGT
TTCATCATTAATTTTTTTCATCAGGCCTATTTTGACACTGCGTTTTATTTAAATAAAATT
TTACTGCCCTTTGCTATGAAGAGTGTCATTCTGGCTGTTTTAAGTCGGCTAATTTCAAAT
TAAATTAAACTTATAAAAAACCTATATTATACCGGCATTTATACTACCAAATAAATGCTT
TCTGGCTGTTTTAAGTCGGCTAATTTCAAATTAGATTAAACTTATAAAAAACATATATTA
TACCGGTATTTATAATACCAAATAAAATGCTATTAGATTCATCGTTAAATACGATTTTGT
TATATTGGTAGCGTTCGATCCGCGCGTTGCAGTTGCAGGGTGTGAACCTTCGCTGGAACA
CCCCAGTTAACATTATTGAATATACCTCGCTAATAAAAATATCGAAATGATCTACCATAG
CTGAAACATTAAATTCATAGTGTTGTCTAAGAACACTATCAAATTAAGCATCCAGGTGCA
TGCACGCATCATCGTTTACTTCAAGAAACCATCTGACTGCCGTTGGTCGACATTGGACT
TTTATTGTTTTTTTTTTCTTACAGACTGCCACCTAATAATAAACCTCCTTTTTTTTCTTT
TCTTTTCTTCCCTTGAGTGACTGATTGAAGAAGGAAACTGGCCGAATAAACAACGAGCTC
TCGTTAGGTCGTGAGGAGATGCATGCAAAGGTTAGTTGCCCCGAGGAGATGCTTATGCA
AGTTCCAGAGTACTCTTTGTTTGCTGCAAGTTGTTGGTGTTGGCTTTGTTTTTTTCCTT
TTTCGTTTCCGTTCCGTTTGCTGGTAGTATTGTGTGCGTGTCCGAGTCTTGGAGGCATCA
AGGCAAGCCCGTTCTTGCAAGAAAGGGCATCGTCGCTGTGTTTTTTTCCCCTCCCAAG
TCTTGGAGGCACTGTTTGTTGGCTTGGCCAGTACTACTAGCGCACTCACGTTGCGTACGA
TCCCTCTCGTGAGGTGTGCGGCTTTGAGCCGTCAGTTTTCCACGGCCAGCCCCAGCCCCA
CTCCTCGCCGCCGAGACGGACGGAAACTGCAAATCAAATGTGTGTGTAGGACCGGGAC
CGAGCACGACGACACGGAACCTACTTGCACCAGCAACCAGCGCTGAATACGCCGTACGTG
TTCTTTTAAGATACGCGTAGAAGAAAATCATGCACGAGAATGAATGGAAATAGAGAGGGA
GGGGGGCACACAGCACGGCCCGGCCTGATCCTGATGCCGACAGTACAAGGCTTACGGTGT
AGTAGTAGTGTACGTGTACCCTTGCATTGGTATACTAGTGCACTGATACATGGAAAATAT
```

FIG. 4 (continued)

```
ATTAATCTCAAATGTTTTCACTAATCCTACACGAAGCCAAGCCACCTACCGGTCTCTGAA
TCAGAACACCCCTCTCTGCTAGACAACGCAGCGATAGAGATGGGGGGAAACTAACTCCTG
CCTGTGCTGTGCGTGCGTGCTTGCGTTGCGTCTGCATGCATCCGGATATGCATTGCAGTT
GCAGGCGGCGTTTCCTTTCGCAGGCCCGGGCGTTCGATTGCCTCTTCTGGATTGAAGCGT
GCAAGAGCCATGACCGTCGTTGCGGCGTGGATGGATCACGGATGGGAGGAGCGCAGCAGC
GGACGGACGGAGTACCAAGAAAAAAGAGATCCAGCCGGAAGCCCAGGGAAAAGCGACGGA
TAACCTACCGAAATTGGGGAAGACAACGACGGCTTGTTTCTACGTAAAAGACGGCTACAG
GCAACACCCATTTACGACGACGACGACCTGACTTGCACAAGCAGATGAGCTGTGTTGCCT
ACCCGTGGTTTAAAACTGTCAGGTTGGTCTTGCTCGTTTCTGGTTTCTACCAGCAATTTC
AGACCAGTCTTTATATTTTTTTTCTTGCAAAAACTACCAGGACTTACTATATATGTATG
TCTCATAGCGTGAACCGTGAGCGGGTTTCATCGGTCTGTGGGTTCAAGAACACTTCACTA
TATATAGTCTGTAAATGATGAGCCCATGCCACACTCAGTTGCAGCAAAACTAATAAAAAA
AACGATGGCGCAGAACATTTGCAGCAAAGCAAGCTAAAGGAGAGAAACCTCATATACTTG
CACTTTCGTCATAATCGTAAGATCAGAAAAAAAATGCAACAAACATGACACGGTATCGTT
CCAGTACCAGCCACCAGCGGTCTTACATAGGAGTAATAATCAGTACAGCTTCAGATGATG
GCGCATGTAATATTTGCGCCATATCTACCTAGCACACGACCTACTCCAATTTTTCACGAG
ATGGGTCGCACGATCTCTATGGGGGGCAAGAATCGAGTCGCCATGTGACATACGTGCAGC
AGTATCACGGAATGAATTTCAGCTCGCAGTCGCAGTCGCAGGCCTAAACGCTAATGATGG
TCAGCTTAGCAGAGGAGAGCTCTGCTTGAAACACACAGCCCACACACAGGTCTTGGTACC
ACCACCACCTATGTACAAAAATACCAGCCCTTGCAGATCACCAGGGACGGGCTAGAACTC
AGCCTTCGCCTGATCAGCTTGCAACTGGCCTGCATCACATACATATACAGCAACACATGG
TTGGGTTATCAGTCAAATAATGGTAATCTCCCGAATGGTGCGCGCTTCAATTGATCGTCC
ATCACTCACATACCATCAAAGGTCGGGTACTAAAAGCCCATCCTCCTCCTGCCTTTGCTC
GCTACCGGTAGTAGGGGTAGGCAAAGCATGCTGTAGGCCATCCTCCCACAAGTCCCTTTG
CTGAGAAATATGCCAGAACTGTTATAAGATCCATATTGACAGCCATTAACTAGCTATACA
GATTGCTGATTCCTCGGGCAAACATTTCTACCTGCTTTTGAAAAGCAAACTGTGGGCTGG
CCGCGTGGGGCAGAGCCGTGTCTAGCAGCAGGCTTAGAGAGCACTGATCCTCCATACCAC
TACCGCTACCGCTACCACCCGAGCCAAAGCTGTGGAAAAGATCCGCCTGCTCGCAGAATG
GAAAAGCTGCGCCGGCGCTTTCCAGTGGAAAGACCGAACTTGCCGAAGGGCCACCACATG
GCTGTTGGTACATCTGAATTAACCAGGATAAAATAGCGTGTGTCAAGGGCGGATTTGATG
TGCAGGTACAGAGCATCGGAGATTGATGTGTGGGTCAAGCTCACGTCTTTGTGCAGGAGT
GTCGATAGGTTGCTGAAATCAAGCTCTGGGTTCACAGTGGCGAGCTTCATGGACAGGAAC
TGAATAAAAGTAGTGTTAATAAACAGCAAAAGAAAAAAAAAACGATTGGAATCTCGAGCT
ATGACTGTGTTATTATGTAACCAAATGTAAGTGGAACCCTCGCCTCACCTCAACTTGCTG
CTGCAGCGACTGGACGTAGTTTATGATCTCATCGAGCATGAGTGCCTTGCCGACCACCTA
CAGTAGGGAATCCCGTCAAATTACAGGCAGCAATTGACACTTACACACGACAATTCACTG
TCCAAGAACTCCATGGCCATACCTTGTTGCATCCTGGCACTAGGTCCTGTAGAAATTTCA
TCCTCTGGCTAATCTTCTCTCTTCTAACCTATCAAGACACAAATAACAAAAGTGTGGTTG
TGAATTCAAACCCGAAGCACAAAATTTCCATTTTGCGATTTAGCCCAAACGGTAGGTAGA
AATGGAATTGCAGTGTCTTACCCTCTCTGCAAGGCTGTGGCTGTCAGTCGCCTGCCCCCG
CCGCGCCCGGACATGGACGTAGTCTTTGGGCGGTTCGACTGCCGGCTTCGAGCTCTTCCC
CTTGCCCTTCTTCTGCGCTTTGACTTCAACCAAGGCGTCGCTCGCCGCCGCCTCCTCCTC
CTCTTCCTTCGGCTTCACCGGACTGTCGCTGGCACCCACTACTCTGCACCTCTTCCCGTC
CGGACCCTTGGCCTCCGCAACCTGCAAACCAATATCGAGAATGGCGGCACCGGCACGTCA
AGAACCAGCAAGCTAAATTCAAAGCACAGTCCACTGCGCACAGTCGTTTCGTTTCCGCAC
CTTGCTCAAGCAGGCCTCCTTGCCACCGGCGGACCCCGTGGGCGGCGCCTTGCGTTTCCT
GGCATTGCCGTAGTCCCTAGCGCGCGCCCACGCTGGGTCGGACACCGACGACCCCTCCGG
AGACCCGCCGCCACACCCTGCCTCCGCGGGCACCCCGAAGAGGCCCCGCCGCCGCCGCC
GCGTAGCGTGTCGAGGAACCCGGCGTCCAGCGCGGCGAAGCTGAGTGCAGGGGCGGATGA
GCCCATGAGCAGGCTGGCAATGTAGTCGCTGTCCATTGAAACAAACAAAGGCGCTGCCGC
AGGAATTGCGCAGGAAGCAAAGGGAGGGTGAGGAAGTCTTGGGTCGTCTCTCGTCTACTG
CGAGCTCGAGTCTGCAATGGATTTGGGGGAAAGCGAAGCGACCGAGGCCGCGGAACCGGT
AGGTGGGGGATTGCTTTATAGAGCGGTTGTTGCCGCTGCGGTTGGGTTGTGGGCCGCGCG
CCGCATCCGTCGCGTAGCTCGGCGCGGTGGGATGCTTGCGGCGGTGGGTTACCACCGGGT
TATACTGCGGCGGCGCTCGCGCAGGAGAGGGGAGAAAAGGCGGTCAAAACGGGACGGAGC
GGGCGGAGGTGTAACCGTGTAGCCACCGCGCTCCGCCGGCAGGCCGAGCAAATGACGGTC
```

FIG. 4 (continued)

```
TCTGGCAGCTCACCATTGAGGGGCAGTGCTCCGGGATTTATGGCTTGGGAGAAAGACGTT
TCTGTCCCCTCTGTTAACGCATCAGGGAAGGTGCTCTCCGGCGTGTTGACAGCCTACACT
CGACCGTGAAAGAATTCATAAAATATGCCGTCTTCTAGGTTGAGTAGTTTGCGGTGCGGA
TCCAATTACATAAATAAATATATAAGAAAAATACTATGAAAGATAGATCTATGGGCACGA
GGCAAGGACACAAACGTAAGACTAGAAAGAAGGCCTATCACGAGAATAATTTTAGAAAGA
TAAACATAATAAAGATATTATCAGATTAGGAGATATGATCTGAAACCAAATAGATATATA
AAGATCCATATAGGTAAAAGAAAACACCATAAAAACAAAGTTTGACTCCTTGTTAGATCG
TGATAGACTCGATTATGTGTCTTATCATACAATCCACCTAGATACACTTTTGCGAACCAT
TGTATTTCCTTGGACTATATAAAAGAAGGACCGAGGGTGCCCCACGAAGACAGAAGAGAT
CATTAGATAAGAATATGAATACCGGCACAAAACGGGACGTAGGGCATTATCTAATCTCAA
AAGTATAAACTTGTATAAATCTTAGTGTCTTTTGTGCCTTTAGCTTTAGATTTAGCTTTT
GATTACGTGACCTACCCCATAAAATCACTATCGAATCAGATTTTATAGTTGGTGCGCTAG
GTAGGGGTAGCCACACTAATCAACAAAGAGTTGATGGCAACCATATGTTTCACATTAGAA
GGAGAAATCATCTTCAACACCCAGAGATCTATCGATGGCTTGCTCTAGTGGCTTTGGCAT
CATATGACCAAAATCCCGAGGATACAATATTCATCTTGGCAAATCTAGGTCAATTTGATA
TCATGATATCTACTCGAACTCGAATTGGACTTCAATCATGGTTCGAACTTGTACATGAGT
CTAAGTTGGACTATGACTCCAACCCTAACTTGGATTCGGGCCCAGACTCGAACCTATAGA
ATCCATTTAAAGATTGCTTCGAGATCATGGTTGCTTCGACGATAAGATTGCTTCGAATGG
TTCGCGACCTTAGCATGGACGATCCGCTCCTCGCACAACGGTCTAATTTGATAGCCCGAC
GGCTATGACTAATAATCTAACGGTTATGAATGACATATCAACGACTCTCTATCCTTGGTG
ATTTGACGTGGACGGTCTATCCTTCGGACTGAGCAAAAATACCACTAGCGAGCAATCTGT
GAATTATGGTGGGATGGTCCACACAAGGACCCAAACAATACGTAGCTTAGGCTAGACGGT
CCATAGTTCAAATTTATGAAACCACAAGTTCATGTGTGTCTTCTGATCATAGTACTCCGG
ACGGTCTAGCATTAGCGTCGGATGATCCATGCTTGGCAATTTTAGAACTTGAGTTTTTGT
ATATTTGTCCATCTTCAAAGTATCTTCTCCAAGTGGATCTTTGGGTGTTCCTATGATTTA
GACAACCATATCTAGAGACTTTCCAACTAGTCCAAGTCACAGAATTTGGTCATTTTAATT
CATCTAACTCATAGCCTGATTCTTGCTCAATCTTAGCTCCAAAAGAGTGAATCTTTGAAT
CTGAGCATTCCAACCTCCCTAGATAGATTAAATAGTTTCTATGGGTGTTAAGAATTCATC
CAAAGTGTAGAACTAATGTAAGTTCTTCTTTTCCAAATACTTGGCAAACTTGGTAGTCCA
AATGGTTGTGATGGTCATCAAGCACCAAAACAAGTCTAGAAATGGATTAAGCCCCATTTC
ACTTCCACTCCATCTCTGAGATAATCACAAGAAGTATATTGAACCAAGGCTAGGGCACTA
AGAAGCCACTACTAGAGGTTAGTCAACATCTCCTTGTATTCACATCTATGTAACAAGGTC
CTCCTCATAATGTCGTTCAAGAGATGAATCGCTGGTGTAAGCTCACTAGGTTGTATCTGG
AGCAGTCTTAGAATGGTGGCCTAAAGCAGGCTACTACGTGGAATGTCCCTAGGAGCTCTC
CACCTTGAGGGCATCTAGGTGGATCCATAGTATCATAGCATGGGTTGTGAAGATGTGTGG
TTGACTCTATAAACCCAACTCTCGCTTTGGTAGCATTAGCATATAGTCTATGTGGCTTGC
CTCTAAAGGCAAACTAAAATTACTCATAGTCAAGGTGGATCTAAAGTGAGGCATAGAACT
CTCTGACTCAGGCCTCAACTTATAAGCCAATCATCCCAAACAATTTGTCAGTCTTGGTAG
ATAAGTGAGGTAGGGATGAATCTAGTATCCTCAGCAACAACGATGTCCTCTAAGGAACAA
ACTCGATGAGGTATGAGGGGTGATCCAATGTGAGTCATGGTTGAGTAGAAGTCCTCCTGC
AGCAAGTCTATAAATTGTCTGATGCTCTAGGGTCCCCTACTGCTAGAAACCACTACTCTA
CTGGCACAAAGCGGAGCTCCTATACTCATGGTCCTTAGGTCAAGGTAAATAACTAGTGGA
TGTGAGAGCACCTAGAGGGGGTGAATAGGTGATCCTGTGAAACTTGAAAACTTAATGCC
ACAAAACTTGGTTAGGCGTTAGCACAATAATGCCAAGTGGCTAGAGAGGAGTCTCAACAA
AACACAATAACCACAAGAGATCAATCACAGAGATGGCACAGTGGTTTATCCCGTGGTTCG
GCCAAGACCAACGCTTGCCTACTCCACGTTGTGGCGTCCCAACGGACGAGGATTGCAATC
AACCCCTCTCAAGCGGTCCAAAGACATACTTGAATACCATGGTGTTTGCTTTTCTTTTCT
ATATCCCGTTCGTGAGGAATCTCCACAACTTGGAGTCTCTCGCCCTTACAAAGATGTTCA
CAAAGAAGCACGGAGTAAGGTAGGGATTAGCAACTCACACAAGACACAAAGATCACGGCA
AATACGCACACACAAGACCCAGACTTAAGCTCAAGAGACTAGCACACTAGAACGGAGCTC
AAATCACTAGAATGTCGAACAAGTGCGCAAGAATGGAGTGTGAGTGATCAAGATTGCTCA
AGGAATGCTTGGTGTACTCCTCCATGTGCCTAGAGGTCCCTTTTATAGCCCAAGGCAGC
TAGGAGCCGTTGAGAGCAATCCGGGAAGGCAATTCTTGCCTTCTGTCGCCTGGTGCACCG
AACAGTCCGGTGCACCACCGGACACTGTCCGGTGCGGATTTCCTTCCTTATTTGGCGAAG
CCGACCGTTGGCAGCCTTGGAGCCGTTGGCGCACCGGACACTGTCCGGTGCACACCGGAC
AGTCCGGTGCCCCCTCCCGACCGTTGGCTCGGCCACGTGTCTCGCGCGGATCGCGCGACC
```

FIG. 4 (continued)

```
GACCGTTGGCCCGGCCGACCGTTGGCTCACCGGACAGTCCGGTGAATTATAGTCGTATGT
TGGGGACTTGTTCTCAAATGCTATGAGTTAAGAACAAGGCAACACAGAAAATGTTAAATG
GTAAAGTCCTTCGTCCTTCGAAGCATTATTTCCCTTAGGATATAATGATTTTCGGACGAA
GGTTATGAAGGGCGCACCTTCATAAACACAACATACGATGATGAAGAATGAACCATATGA
AATATCAAGAATAACATAAACAATTATATGTTATTATCAACTTATTTTTGCATTATTATT
ATGAAGAAATAGAAATGACATCAAATTACAACTGTACCTTCGGCTTGGAAGGAGATGAAA
ATACAAGTGTGACGCAAAAGCAAATGCCAAGTCAGCGTAAACAGTACGGGGGTACTGTTC
ACCTATTTATAGGCACGGGACACAGCCCATATAAAATTACATTCATGCCCTTTACATTTG
GTAGTAATTCTATAGTAATCCACCGAGGTCTGAATAGCCTTTTCATCTTTAAGTCGGTTT
CTTTTTCTGCTACCACGCCGAAGCTTTCCCGCTCACATCTTCGGCGTTGTATCAACCTTC
GTATTACTTTGGGCTTCTCCTACTGTGATATCGACTCGAGTCCGAAGATACCTATTCACA
CATTATACTCCAGAAACACTGTTAAATCCTGTTTTTGAGGACCTTCGGAAGCCGAAGGCC
CCCAACAGTAGCCCCTCGCAATATAAATTTGTTAAAATAATAAATTTAGATTGCGACATG
TACGAAGACTTTAAGCCTAAGGTCCGAAAAAACACCTTCCTTTTGCTAGAATAGCAACAT
TCACTGACAAGCGGGGTCTTTCAATTTTTAACGCACTGGGCGTATAAATAAGAGCATACC
GCGAGCTCATTTGGCACGCTCTCTTGCCATCTGCTCTCGCTCACTCAATTTTTAGCTCTT
GCGCACCGAGATTTGCTTAGCTTTTTAAGTTTTTAAGCTTCGGCGCTGAAAACAGTTTTT
TAGTGTTTCCGAAGATGTCTGAAGATAAGAAGGCTGCTCTCGAGATGAAGCTGAGTCTCT
CTGAAGAGAAGAACCTGGGGTTTCTTATAGCAATGTCGAAGACCAACACAGAAAAAATCA
CCAAAGAGATTTTAGAAGGTTTGTCTGAAGATACTGATGACAGCGACAATTATGATGTAG
ATAGTGGTGGTGAAGACTCCGAAGATCGCCCCTGGCGACCAAGCCATTCAGTTTTTAGCA
AATCAGGTATCAAAGAAAATCATCTTGTCAACATGAGGGGAAGATACTTCCGGGATTTAT
CCATTGTGAGGGTCGACGAAGGAGAGAAGACTTGCCCGACCTCTGAGGAAAATGAAGTCG
TAGTGTTCCGAAGCTTTTTGAAAGCTGGACTACGATTTCCTTTGAGCAGCTTTGTCGTAG
AAGTGCTGAAAATGTTTGAAGTCTATCTTCATCAACTTACCCCCGAAGCAATTATAAGGC
TGAATATCTTCGTGTGGGCCGTGAGAAGCCAAGGTCTGGAACCTGATGCGAAAAGTTTCT
GCAACATACACGAATTATCATACGAGACAA
```

MaizeGDB version 4.0 reference sequence display of gene model Zm0001d006065 which corresponds to GRMZM2G083504 in versions 2 and 3 of the maize genome annotation.

Maize B73 Genome Reference history figure from MaizeGDB.

TARGETED MODIFICATION OF MAIZE ROOTS TO ENHANCE ABIOTIC STRESS TOLERANCE

CROSS-REFERENCE TO RELATED APPLICATIONS

This application claims priority to U.S. provisional application No. 62/395,434, filed Sep. 16, 2016, which is incorporated by reference herein and relied on in its entirety.

STATEMENT AS TO RIGHTS TO INVENTIONS MADE UNDER FEDERALLY SPONSORED RESEARCH AND DEVELOPMENT

This invention was made with government support under IOS0965380 awarded by the National Science Foundation, 2014-67013-21572 awarded by the USDA/NIFA, and Hatch Act Project No. PEN04548 awarded by the USDA/NIFA. The government has certain rights in the invention.

FIELD OF THE INVENTION

The present invention relates to crop breeding. More particularly, the present invention relates to targeted modification of maize root to enhance abiotic stress tolerance.

BACKGROUND OF THE INVENTION

Improvements in the yield of cereal crops such as wheat and maize have recently plateaued (Grassini, P., Eskridge, K. M. & Cassman, K. G. Distinguishing between yield advances and yield plateaus in historical crop production trends. Nat. Commun. 4, 2918 (2013)). This is a major cause for concern with respect to food security, particularly given projected global population growth and the impacts of climate change on crop productivity. In intensive agricultural systems, intensive fertilization and irrigation cause environmental degradation and are not sustainable in the long term, while in the low-input agriculture characteristic of developing nations, limited availability of water and nutrients are primary limitations to crop production (Sutton, M. A. et al. Too much of a good thing. Nature 472, 159-161 (2011), Lynch, J. P. Roots of the second green revolution. Aust. J. Bot. 55, 493-512 (2007)). Therefore, crops and crop varieties with greater resource efficiency and climate resilience are urgently needed in global agriculture.

Anatomical traits have the potential to deliver major improvements in crop production, by improving resource capture, transport, and utilization (Lynch, J. P. Root phenes that reduce the metabolic costs of soil exploration: opportunities for 21st century agriculture. Plant. Cell Environ. 1775-1784 (2014), Postma, J. A. & Lynch, J. P. Root cortical aerenchyma enhances growth of Zea mays L. on soils with suboptimal availability of nitrogen, phosphorus and potassium. Plant Physiol. 156, 1190-1201 (2011)). For example, smaller diameter of xylem vessels improved water use efficiency, conserving water resources for grain filling in wheat (Richards & Passioura. A breeding program to reduce the diameter of the major xylem vessel in the seminal roots of wheat and its effect on grain yield in rain-fed environments. Aust. J. Agric. Res. 40, 943-950 (1989)). Reduced cortical cell file number and increased cortical cell size reduce root respiration and increase rooting depth, leading to improved water acquisition and greater yield under drought (Chimungu, J. G., Brown, K. M. & Lynch, J. P. Reduced root cortical cell file number improves drought tolerance in maize. Plant Physiol. 166, 1943-1955 (2014), Chimungu, J. G., Brown, K. M. & Lynch, J. P. Large root cortical cell size improves drought tolerance in maize. Plant Physiol. 166, 2166-2178 (2014)). The formation of root cortical aerenchyma (RCA), which converts living cortical cells to air space via programmed cell death, also improves crop growth and productivity under drought and suboptimal nitrogen conditions (Saengwilai, P., Nord, E., Chimungu, J., Brown, K. & Lynch, J. Root cortical aerenchyma enhances nitrogen acquisition from low nitrogen soils in maize (Zea mays L.). Plant Physiol. 166, 726-735 (2014), Chimungu, J. G. et al. Utility of root cortical aerenchyma under water limited conditions in tropical maize (Zea mays L.). Field Crops Res 171, 86-98 (2015)). Root anatomical traits, therefore, represent promising targets for crop breeding.

Despite this knowledge, anatomical traits have received little attention as selection criteria in plant breeding because of the challenges of sampling root systems from soil and quantifying anatomical phenotypes. Instead, genetic and physiological studies of root anatomical traits have been limited to artificial growth conditions, young plants, and few replications due to difficulties in obtaining and analyzing root cross-sectional images in a large number of samples. However, the recent development of high throughput phenotyping image analysis software, RootScan, permits quantitative measurements of anatomical traits from root cross-sectional images (Burton, A. L., Williams, M., Lynch, J. P. & Brown, K. M. RootScan: Software for high-throughput analysis of root anatomical traits. Plant Soil 357, 189-203 (2012)).

In view of the current state of the crop breeding industry, particularly new maize varieties, it can be appreciated that identifying genes conveying abiotic stress tolerance is a substantial challenge in the field. Accordingly, a need exists in the field to identify additional genes that influence stress tolerance.

SUMMARY OF THE INVENTION

This invention is based, in part, on the inventors' discovery of a maize gene named GRMZM2G083504 (a basic helix-loop-helix transcription factor) in version 3 of the maize genome annotation and named Zm00001d006065 in version 4.0 of the maize genome annotation. (Note: Use of either of these terms in this document are used to indicate the same gene.) This gene affects the amount of root cortical aerenchyma (RCA). Aerenchyma are air spaces in plant tissues due to programmed cell death of cortical cells. Root systems with more RCA are metabolically less expensive so that more extensive and deeper root systems can be grown with a lower carbon cost to the plant. Therefore, stress tolerant plants with more effective root systems can be grown with little penalty on grain or stover yield. The inventors have demonstrated in the Examples that a reduction of gene function results in decreased aerenchyma. Accordingly, this invention has value as an approach to improve yield under stress tolerance and increase soil carbon sequestration.

In a first aspect, the present invention provides a recombinant maize plant tolerant of abiotic stress comprising a non-natural mutation that modifies the function of maize gene GRMZM2G083504.

In one aspect, the present invention provides recombinant maize plant tolerant of abiotic stress comprising a non-natural mutation that increases the function of maize gene GRMZM2G083504, wherein the recombinant maize plant exhibits increased root cortical aerenchyma (RCA) and increased abiotic stress tolerance as compared to a maize plant lacking the mutation.

In another aspect, the invention is directed to a method of increasing abiotic stress tolerance in maize, comprising introducing in maize a non-natural mutation that increases the function of maize gene GRMZM2G083504, wherein the maize exhibits increased abiotic stress tolerance as compared to maize lacking the mutation.

In another aspect, the invention provides, a method of increasing root cortical aerenchyma (RCA) in maize, comprising introducing in maize a non-natural variant that increases the function of maize gene GRMZM2G083504, wherein the maize exhibits increased root cortical aerenchyma (RCA) as compared to maize lacking said variant.

In another aspect, the invention provides, a method of decreasing root cortical aerenchyma (RCA) in maize, comprising introducing in maize a non-natural variant that decreases the function of maize gene GRMZM2G083504, wherein the maize exhibits decreased root cortical aerenchyma (RCA) as compared to maize lacking said variant.

In another embodiment, the invention encompasses a method of identifying an abiotic stress tolerant maize plant, comprising: (a) assaying expression levels of a maize gene GRMZM2G083504 in maize plants; and (b) selecting a maize plant having an increased level of maize gene GRMZM2G083504 expression, wherein the selected maize plant exhibits increased abiotic stress tolerance as compared to a maize plant not having the increased level of maize gene GRMZM2G083504 expression.

In another embodiment, the invention is directed to a method for providing an abiotic stress tolerant maize plant variety, comprising: (a) assaying expression levels of maize gene GRMZM2G083504 in maize plants; (b) selecting a maize plant exhibiting increased levels of maize gene GRMZM2G083504 expression; and (c) breeding the selected maize plant exhibiting increased levels of maize gene GRMZM2G083504 to yield a maize plant variety providing increased tolerance to abiotic stress.

Other objects, features and advantages of the present invention will become apparent after review of the specification, claims and drawings. The detailed description and examples enhance the understanding of the invention, but are not intended to limit the scope of the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 illustrates spatial and temporal expression of bHLH121 identified by GWAS based on the maize B73 gene atlas.

FIG. 4 is the nucleic acid sequence for the version 4.0 sequence for the genomic sequence of the Zm0001d006065 gene model (SEQ ID NO:1) and a sequence that includes this genomic sequence plus 5 kb on either side that should capture primary promoter and enhancer elements (SEQ ID NO: 5).

DETAILED DESCRIPTION OF THE INVENTION

Figures 1A, 1B, 1C, 1D, 1E, 1F:
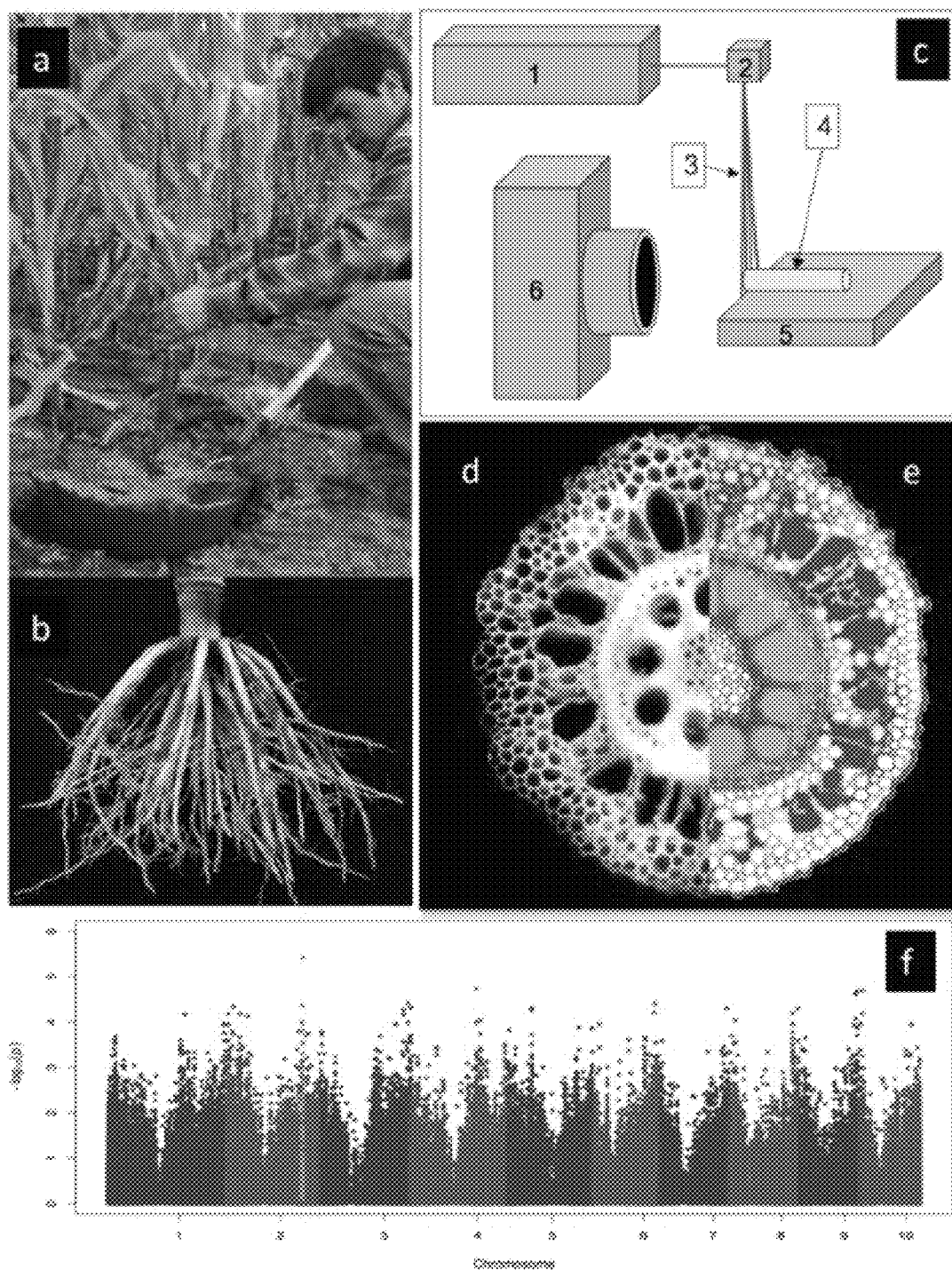
FIGS. 1A-1F illustrates an anatomics pipeline for maize: a) Root excavation. b) A clean maize crown root. c) a schematic of LAT: the laser (1) beam is controlled by galvoscanner (2) to create an ablation plane (3), the root sample (4) is advanced into ablation plane (3) by a computer controlled movable stage (5); the ablated face of root sample is imaged by camera (6). d) An image of a root cross sectional surface captured by LAT. e) Root anatomical traits were quantified by RootScan software. f) Genome-wide association study was performed on the Anatomics data.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention, which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); and Handbook Of Experimental Immunology, Volumes I-IV (D. M. Weir and C. C. Blackwell, eds., 1986).

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters that cause a gene to be expressed in most cell types at most times are commonly referred to as "constitutive promoters". Promoters that allow the selective expression of a gene in most cell types are referred to as "inducible promoters".

A "host cell" is a cell which has been transformed or transfected, or is capable of transformation or transfection by an exogenous polynucleotide sequence. A host cell that has been transformed or transfected may be more specifically referred to as a "recombinant host cell".

The nucleic acid sequence for the target gene, GRMZM2G083504, is recited in SEQ ID NO: 1 and also recited in FIG. 4.

By "modulation" of the target gene, we mean to include both over-expression and under-expression. In a preferred version of the present invention, the gene is over-expressed. By "modulation of the gene," we also mean to include modification or manipulation of the regulatory regions of the target gene.

By "a non-natural mutation," we mean to include all manner of recombinant and transgenic manipulation to the plant. For example, a plant comprising an extra copy of the target gene has a non-natural mutation. A plant comprising a vector containing the target gene and a promoter from a different maize or plant line is a non-natural mutation. We also mean to include modification or manipulation of the regulatory regions of the target gene or of any region that is contiguous with the target gene up to 5 KB on either side of the target sequence.

A polypeptide "substantially identical" to a comparative polypeptide varies from the comparative polypeptide, but has at least 80%, preferably at least 85%, more preferably at least 90%, and yet more preferably at least 95% sequence identity at the amino acid level over the complete amino acid sequence, and retains substantially the same biological function as the corresponding polypeptide to which comparison is made.

The term "substantial sequence homology" refers to DNA or RNA sequences that have de minimus sequence variations from, and retain substantially the same biological functions as the corresponding sequences to which comparison is made.

As used herein, "hybridizes under stringent conditions" is intended to describe conditions for hybridization and washing under which nucleotide sequences that are significantly identical or homologous to each other remain hybridized to each other. Such stringent conditions are known to those skilled in the art and can be found in Current Protocols in Molecular Biology, Ausubel et al., eds., John Wiley & Sons, Inc. (1995), sections 2, 4 and 6. Additional stringent conditions can be found in Molecular Cloning: A Laboratory Manual, Sambrook et al., Cold Spring Harbor Press, Cold Spring Harbor, N.Y. (1989), chapters 7, 9 and 11. A preferred, non-limiting example of stringent hybridization conditions includes hybridization in 4× sodium chlorine/sodium citrate (SSC), at about 65-70° C. (or hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or hybridization in 4×SSC plus 50% formamide at about 42-50° C.) followed by one or more washes in 0.3×SSC, at about 65-70° C. A preferred, non-limiting example of highly stringent hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15 M NaCl, 10 mM $NaH_2PO_4$, and 1.25 mM EDTA, pH 7.4) can be substituted for SSC (1×SSPE is 0.15 M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$ (° C.)=2(# of A+T bases)+4(# of G+C bases). For hybrids between 18 and 49 base pairs in length, $T_m$ (° C.)=81.5+16.6($\log_{10}$[Na+])+0.41(% G+C)−(600/N), where N is the number of bases in the hybrid, and [Na+] is the concentration of sodium ions in the hybridization buffer ([Na+] for 1×SSC=0.165 M). It will also be recognized by the skilled practitioner that additional reagents may be added to the hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS) chelating agents (e.g., EDTA), Ficoll, PVP and the like. When using nylon membranes, in particular, an additional preferred, non-limiting example of stringent hybridization conditions is hybridization in 0.25-0.5M $NaH_2PO_4$, 7% SDS at about 65° C., followed by one or more washed at 0.02M $NaH_2PO_4$, 1% SDS at 65° C., see e.g., Church and Gilbert (1984) Proc. Natl. Acad. Sci. USA 81: 1991-1995, (or alternatively 0.2×SSC, 1% SDS).

"Polynucleotide (s)" generally refers to any polyribonucleotide or polydeoxribonucleotide, which may be unmodified RNA or DNA or modified RNA or DNA. "Polynucleotide (s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. As used herein, the term "polynucleotide (s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

The term "isolated nucleic acid" used in the specification and claims means a nucleic acid isolated from its natural environment or prepared using synthetic methods such as those known to one of ordinary skill in the art. Complete purification is not required in either case. The nucleic acids of the invention can be isolated and purified from normally associated material in conventional ways such that in the purified preparation the nucleic acid is the predominant species in the preparation. At the very least, the degree of purification is such that the extraneous material in the preparation does not interfere with use of the nucleic acid of the invention in the manner disclosed herein. The nucleic acid is preferably at least about 85% pure, more preferably at least about 95% pure and most preferably at least about 99% pure.

Further, an isolated nucleic acid has a structure that is not identical to that of any naturally occurring nucleic acid or to that of any fragment of a naturally occurring genomic nucleic acid spanning more than three separate genes. An isolated nucleic acid also includes, without limitation, (a) a nucleic acid having a sequence of a naturally occurring genomic or extrachromosomal nucleic acid molecule but which is not flanked by the coding sequences that flank the sequence in its natural position; (b) a nucleic acid incorporated into a vector or into a prokaryote or eukaryote genome such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene. Specifically excluded from this definition are nucleic acids present in mixtures of clones, e.g., as those occurring in a DNA library such as a cDNA or genomic DNA library. An isolated nucleic acid can be modified or unmodified DNA or RNA, whether fully or partially single-stranded or double-stranded or even triple-stranded. A nucleic acid can be chemically or enzymatically modified and can include so-called non-standard bases such as inosine, as described in a preceding definition.

The term "operably linked" means that the linkage (e.g., DNA segment) between the DNA segments so linked is such that the described effect of one of the linked segments on the other is capable of occurring. "Linked" shall refer to physically adjoined segments and, more broadly, to segments which are spatially contained relative to each other such that the described effect is capable of occurring (e.g., DNA segments may be present on two separate plasmids but contained within a cell such that the described effect is nonetheless achieved). Effecting operable linkages for the various purposes stated herein is well within the skill of those of ordinary skill in the art, particularly with the teaching of the instant specification.

As used herein the term "gene product" shall refer to the biochemical material, either RNA or protein, resulting from expression of a gene.

The term "heterologous" is used for any combination of DNA sequences that is not normally found intimately associated in nature (e.g., a green fluorescent protein (GFP) reporter gene operably linked to a SV40 promoter). A "heterologous gene" shall refer to a gene not naturally present in a host cell (e.g., a luciferase gene present in a retinoblastoma cell line).

As used herein, the term "homolog" refers to a gene related to a second gene by descent from a common ancestral DNA sequence. The term, homolog, may apply to the relationship between genes separated by the event of speciation (i.e., orthologs) or to the relationship between genes separated by the event of genetic duplication (i.e., paralogs). "Orthologs" are genes in different species that evolved from a common ancestral gene by speciation. Normally, orthologs retain the same function in the course of evolution. Identification of orthologs is important for reliable prediction of gene function in newly sequenced genomes. "Paralogs" are genes related by duplication within a genome. Orthologs retain the same function in the course of evolution, whereas paralogs evolve new functions, even if these are related to the original one.

The nucleotides that occur in the various nucleotide sequences appearing herein have their usual single-letter designations (A, G, T, C or U) used routinely in the art. In the present specification and claims, references to Greek letters may either be written out as alpha, beta, etc. or the corresponding Greek letter symbols (e.g., α, β, etc.) may sometimes be used.

Nucleic acid constructs useful in the invention may be prepared in conventional ways, by isolating the desired genes from an appropriate host, by synthesizing all or a portion of the genes, or combinations thereof. Similarly, the regulatory signals, the transcriptional and translational initiation and termination regions, may be isolated from a natural source, be synthesized, or combinations thereof. The various fragments may be subjected to endonuclease digestion (restriction), ligation, sequencing, in vitro mutagenesis, primer repair, or the like. The various manipulations are well known in the literature and will be employed to achieve specific purposes.

The various nucleic acids and/or fragments thereof may be combined, cloned, isolated and sequenced in accordance with conventional ways. After each manipulation, the DNA fragment or combination of fragments may be inserted into a cloning vector, the vector transformed into a cloning host, e.g. *Escherichia coli*, the cloning host grown up, lysed, the plasmid isolated and the fragment analyzed by restriction analysis, sequencing, combinations thereof, or the like.

Various vectors may be employed during the course of development of the construct and transformation of host cells. The vectors may include cloning vectors, expression vectors, and vectors providing for integration into the host or the use of bare DNA for transformation and integration. The cloning vector will be characterized, for the most part, by having a replication original functional in the cloning host, a marker for selection of a host containing the cloning vector, may have one or more polylinkers, or additional sequences for insertion, selection, manipulation, ease of sequencing, excision, or the like. In addition, shuttle vectors may be employed, where the vector may have two or more origins of replication, which allows the vector to be replicated in more than one host, e.g. a prokaryotic host and a eukaryotic host.

Expression vectors will usually provide for insertion of a construct which includes the transcriptional and translational initiation region and termination region or the construct may lack one or both of the regulatory regions, which will be provided by the expression vector upon insertion of the sequence encoding the protein product. Thus, the construct may be inserted into a gene having functional transcriptional and translational regions, where the insertion is proximal to the 5'-terminus of the existing gene and the construct comes under the regulatory control of the existing regulatory regions. Normally, it would be desirable for the initiation codon to be 5' of the existing initiation codon, unless a fused product is acceptable, or the initiation codon is out of phase with the existing initiation codon. In other instances, expression vectors exist which have one or more restriction sites between the initiation and termination regulatory regions, so that the structural gene may be inserted at the restriction site(s) and be under the regulatory control of these regions.

Suitable methods for plant transformation for use with the current invention are believed to include virtually any method by which DNA can be introduced into a cell, such as by direct delivery of DNA by PEG-mediated transformation of protoplasts, by desiccation/inhibition-mediated DNA uptake by electroporation, by agitation with silicon carbide fibers, by *Agrobacterium*-mediated transformation, and by acceleration of DNA coated particles. Through the application of techniques such as these, maize cells, as well as those of virtually any other plant species, may be stably transformed, and these cells developed into transgenic plants.

Suitable Maize Lines

We envision that the present invention would be useful in all maize varieties and lines.

Figure 5:
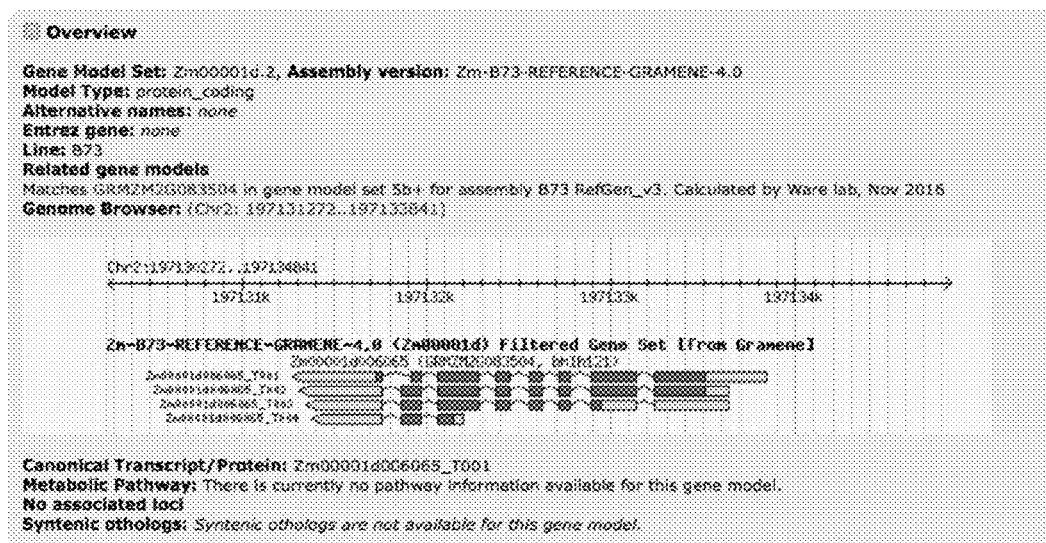
FIG. 5. is a diagram of MaizeGDB version 4.0 reference sequence display of gene model Zm0001d006065 which corresponds to GRMZM2G083504 in versions 2 and 3 of the maize genome annotation.

We note that the conventions of expressing genetic positions in maize have changed. See FIG. 5. Initial work on this invention was done using the Maize B73 reference assembly B73 RefGen_v2 and annotation 5b. Recently, assembly Zm-REFERENCE-GRAMENE-4.0 with annotation Zm001d.2 has become available. The region of interest in this application is largely identical between the two versions, and nomenclature of GRMZM2G083504 from B73 RefGen_v2 annotation 5b and Zm00001d006065 from Zm-REFERENCE-GRAMENE-4.0 annotation Zm001d.2 are considered to be referencing the same gene.

Increase in Gene Expression

The present invention, in certain aspects, includes steps of increasing the function of the target gene to yield a desirable phenotype. To that end, DNA may be introduced into the plant or plant cell to enable over-expression of GRMZM2G083504 and an increase in RCA. Typically, the increase in RCE would be between 1% and 80%. The increase could be quite large in a plant that has no native RCA.

This introduction could include transformation of maize cells with multiple copies of the gene, use of modified or natural promoters designed to over-express the gene, use of constitutive or tissue-specific promoters designed to focus expression is specific tissues or in a non-specific manner, and use of vectors to carry a copy or copies of the gene. One may also wish to transform plant cells with regulatory elements that will modify the native expression of GRMZM2G083504 or modify existing regulatory elements.

Suitable methods for transformation of plant or other cells for use with the current invention are believed to include virtually any method by which DNA can be introduced into a cell, such as by direct delivery of DNA such as by PEG-mediated transformation of protoplasts. These methods and their use are well known in the art. The most likely transgenic approach would typically be using tissue-specific promoters that are stronger than the endogenous version in the line that is targeted.

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

Cells that survive the exposure to the selective agent, or cells that have been scored positive in a screening assay, may be cultured in media that supports regeneration of plants. In an exemplary embodiment, MS media may be modified by including further substances such as growth regulators. Examples of such growth regulators are dicamba and 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, then transferred to media conducive to maturation of embryoids. Cultures are transferred as needed on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins m-2 s-1 of light. Plants may be matured in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants can be grown at a suitable temperature, for instance about 19 to 28° C. After the regenerating plants have reached the stage of shoot and root development, they may be transferred to a greenhouse for further growth and testing.

To confirm the presence of the exogenous DNA or "transgene(s)" in the regenerating plants, a variety of assays may be performed. Such assays include, for example, "molecular biological" assays, such as Southern and northern blotting and PCR™; "biochemical" assays, such as detecting the presence of a protein product, e.g., by immunological means (ELISAs and western blots) or by enzymatic function; plant part assays, such as leaf or root assays; and also, by analyzing the phenotype of the whole regenerated plant.

Very frequently the expression of a gene product is determined by evaluating the phenotypic results of its expression. These assays also may take many forms including but not limited to analyzing changes in the chemical composition, morphology, or physiological properties of the plant. Morphological changes may include ones known to demonstrate enhanced tolerance of abiotic stress, such as presence or absence of root cortical aerenchyma or characterization of root system formation. Most often changes in response of plants or plant parts to imposed treatments are evaluated under carefully controlled conditions termed bioassays.

One would typically assay for a suitable increase in gene expression resulting in increased RCA in the following ways:

Direct analysis of gene expression may be measured by one of various approaches to quantitative polymerase chain reaction, such as digital drop polymerase chain reaction. Variation in root cortical aerenchyma may be measured by microscopic or digital image analysis of sectioned roots collected from plants grown in the field or a controlled environment. The most practical measure of altered abiotic stress tolerance, or altered root system biomass, would be by excavation of all or representative portions of root systems grown in designed stress and control non-stress environments. Yield, yield components, plant biomass, plant health, and other traits would likely be measured in such field trials.

Decrease in Gene Expression

The present invention, in certain aspects, includes steps of reducing the function of a target gene to yield a desirable phenotype, such as increased below-ground biomass as compared to lines with high RCA. To that end, DNA may be introduced into plants for the purpose of expressing RNA transcripts that function to affect plant phenotype yet are not translated into protein. Two examples are antisense RNA and RNA with ribozyme activity. Both may serve possible functions in reducing or eliminating expression of native or introduced plant genes. However, as detailed below, DNA need not be expressed to effect the phenotype of a plant.

Genes may be constructed or isolated, which when transcribed, produce antisense RNA that is complementary to all or part(s) of a targeted messenger RNA(s). The antisense RNA reduces production of the polypeptide product of the messenger RNA. The polypeptide product may be any protein encoded by the plant genome. The aforementioned genes will be referred to as antisense genes. An antisense gene may thus be introduced into a plant by transformation methods to produce a novel transgenic plant with reduced expression of a selected protein of interest.

Genes also may be constructed or isolated, which when transcribed, produce RNA enzymes (ribozymes) which can act as endoribonucleases and catalyze the cleavage of RNA molecules with selected sequences. The cleavage of selected messenger RNAs can result in the reduced production of their encoded polypeptide products. These genes may be used to prepare novel transgenic plants which possess them.

The transgenic plants may possess reduced levels of polypeptides including, but not limited to, the polypeptides cited above.

Ribozymes are RNA-protein complexes that cleave nucleic acids in a site-specific fashion. Ribozymes have specific catalytic domains that possess endonuclease activity. For example, a large number of ribozymes accelerate phosphoester transfer reactions with a high degree of specificity, often cleaving only one of several phosphoesters in an oligonucleotide substrate. This specificity has been attributed to the requirement that the substrate bind via specific base-pairing interactions to the internal guide sequence ("IGS") of the ribozyme prior to chemical reaction.

Several different ribozyme motifs have been described with RNA cleavage activity. Examples include sequences from the Group I self-splicing introns including Tobacco Ringspot Virus, Avocado Sunblotch Viroid, and Lucerne Transient Streak Virus. Sequences from these and related viruses are referred to as hammerhead ribozyme based on a predicted folded secondary structure.

Other suitable ribozymes include sequences from RNase P with RNA cleavage activity, hairpin ribozyme structures and Hepatitis Delta virus based ribozymes. The general design and optimization of ribozyme directed RNA cleavage activity is well understood in the art.

The other variable on ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozyme, the cleavage site is a dinucleotide sequence on the target RNA is a uracil (U) followed by either an adenine, cytosine or uracil (A, C or U). The frequency of this dinucleotide occurring in any given RNA is statistically 3 out of 16. Therefore, for a given target messenger RNA of 1000 bases, 187 dinucleotide cleavage sites are statistically possible.

Designing and testing ribozymes for efficient cleavage of a target RNA is a process well known to those skilled in the art. The identification of operative and preferred sequences for use in down regulating a given gene is simply a matter of preparing and testing a given sequence, and is a routinely practiced "screening" method known to those of skill in the art.

In another approach, it is also possible that genes may be introduced to produce novel transgenic plants which have reduced expression of a native gene product by the mechanism of co-suppression. It has been demonstrated in tobacco, tomato, and *petunia* that expression of the sense transcript of a native gene will reduce or eliminate expression of the native gene in a manner similar to that observed for antisense genes. The introduced gene may encode all or part of the targeted native protein but its translation may not be required for reduction of levels of that native protein.

In another approach, as described in more detail in the Examples herein, DNA elements including those of transposable elements such as Ds, Ac, or Mu, may be inserted into a gene to cause mutations. These DNA elements may be inserted in order to inactivate (or activate) a gene and thereby "tag" a particular trait. In this instance the transposable element does not cause instability of the tagged mutation, because the utility of the element does not depend on its ability to move in the genome. Once a desired trait is tagged, the introduced DNA sequence may be used to clone the corresponding gene, e.g., using the introduced DNA sequence as a PCR primer together with PCR gene cloning techniques (Shapiro, 1983; Dellaporta et al., 1988). Once identified, the entire gene(s) for the particular trait, including control or regulatory regions where desired, may be isolated, cloned and manipulated as desired. The utility of DNA elements introduced into an organism for purposes of gene tagging is independent of the DNA sequence and does not depend on any biological activity of the DNA sequence, i.e., transcription into RNA or translation into protein. The sole function of the DNA element is to disrupt the DNA sequence of a gene.

It is further contemplated that unexpressed DNA sequences, including novel synthetic sequences, could be introduced into cells as proprietary "labels" of those cells and plants and seeds thereof. It would not be necessary for a label DNA element to disrupt the function of a gene endogenous to the host organism, as the sole function of this DNA would be to identify the origin of the organism. For example, one could introduce a unique DNA sequence into a plant and this DNA element would identify all cells, plants, and progeny of these cells as having arisen from that labeled source. It is proposed that inclusion of label DNAs would enable one to distinguish proprietary germplasm or germplasm derived from such, from unlabelled germplasm.

The following experimental data are provided to illustrate the invention. It is to be understood that a person skilled in the art who is familiar with the methods may use other yeast strains, recombinant vectors, and methodology which can be equally used for the purpose of the present invention. These alterations are included in the scope of the invention.

III. EXAMPLES

In this section, the inventors describe various materials, methods and results related to and supportive of the present invention.

Example 1. Targeted Modification of Maize Root Cortical Aerenchyma to Enhance Abiotic Stress Tolerance Anatomics: A High-Throughput Phenotyping Approach for Plant Anatomical Traits Growth of maize root systems in the soil profile can determine their ability to acquire water and nutrients, and also provide anchorage of the plant. Roots that are complex and highly branched have improved acquisition of immobile nutrients such as phosphorus. Roots that are thick and grow deep in the soil acquire water and nutrients more efficiently providing drought tolerance and nitrogen acquisition efficiency. In addition to the value of roots for anchorage and abiotic stress tolerance, the Department of Energy has estimated that increasing root depth in maize by 50% can result in capture of 5 to 10 year-equivalents of US carbon emissions due to the reduced breakdown of plant tissue at depth and the large acreage of maize produced each year.

Anatomical variation represents an underexploited source of traits for crop breeding. The present inventors utilized a novel high-throughput anatomical phenotyping approach (termed Anatomics) that combines laser ablation tomography and image analysis. They employed Anatomics to quantify anatomical variation in roots of ~430 diverse maize lines (Hansey, C. N., Johnson, J. M., Sekhon, R. S., Kaeppler, S. M. & Leon, N. De. Genetic diversity of a maize association population with restricted phenology. *Crop Sci.* 51, 704-715 (2011)). Significant variation was detected for many anatomical traits, including root cortical aerenchyma (RCA) formation, a programmed cell death process that increases soil resource capture by reducing metabolic costs of soil exploration (Lynch, J. P. Root phenes that reduce the metabolic costs of soil exploration: opportunities for 21st century agriculture. Plant. Cell Environ. 1775-1784 (2014)). Genome wide association studies (GWAS) using Anatomics identified a single nucleotide polymorphism (SNP) associated with RCA formation mapping to a root cortex-expressed bHLH transcription factor gene. A transposon mutant in this bHLH gene exhibited reduced RCA formation, validating our GWAS result and providing a new marker for this important root trait.

A significant bottleneck for anatomical analysis has been the low throughput nature of root cross-sectioning and obtaining images for analysis. To address this major bottleneck, the inventors developed the Laser Ablation Tomography (LAT) approach for rapid root sectioning and imaging (see materials and methods). This LAT platform combined a nanosecond pulsed UV laser (Avia 355-7000; Coherent, Santa Clara, Calif.) focused into a beam using a galvanometer scanner for surface ablation of samples. Root segments were secured on the stage perpendicular to the laser beam, moved into the beam at 30 microns per second for 10 seconds while images were captured, and three cross-sectional images per root were saved for analysis. LAT permitted sectioning of over 1,000 root segments and capture of over 10,000 cross-sectional images within 10 working days, which is over 20 times faster than conventional manual sectioning.

The inventors integrated the LAT approach with RootScan image analysis software to create a high-throughput root anatomical phenotyping pipeline that the inventors term Anatomics. The Anatomics approach is designed to facilitate discovery of genes controlling root anatomical traits. To demonstrate its utility, the inventors employed Anatomics in combination with a Genome-Wide Association Study (GWAS) to identify single nucleotide polymorphism (SNP) markers associated with variation in root cortical aerenchyma formation. The study was carried out in 436 field-grown maize lines of the Wisconsin Diversity Panel (WiDiv), which represent a broad range of inbred maize lines (Hansey, C. N., Johnson, J. M., Sekhon, R. S., Kaeppler, S. M. & Leon, N. De. Genetic diversity of a maize association population with restricted phenology. *Crop Sci.* 51, 704-715 (2011)). The inventors quantified root anatomical phenotypes of field-grown maize plants at the flowering stage across three field seasons using the Anatomics platform (FIG. 1). During this study, the LAT platform was used to section over 3,000 root segments and capture of over 30,000 cross-sectional images within 30 working days. RootScan enabled the measurements of 12 root anatomical traits simultaneously at less than 2 min per image. Hence, this novel phenotyping platform is ideal for anatomical research, permitting rapid, precise, quantitative evaluation of the thousands of samples required for genetic analysis and plant breeding.

Anatomics revealed considerable variation for root anatomical traits in lines from the WiDiv maize population (Table 1 below). In general, variation for anatomical phenotypes ranged from 3-fold for the number of cortical cells and metaxylem vessels to 64-fold for aerenchyma area. Substantial variation found in living cortical area, cell size, and cortical cell file number have important consequences for root metabolic costs and therefore soil resource acquisition (Lynch, J. P. Root phenes that reduce the metabolic costs of soil exploration: opportunities for 21st century agriculture. Plant. Cell Environ. 1775-1784 (2014), Chimungu, J. G., Brown, K. M. & Lynch, J. P. Reduced root cortical cell file number improves drought tolerance in maize. Plant Physiol. 166, 1943-1955 (2014), Chimungu, J. G., Brown, K. M. & Lynch, J. P. Large root cortical cell size improves drought tolerance in maize. Plant Physiol. 166, 2166-2178 (2014)). Among anatomical traits, the largest range of variation was found in aerenchyma area and % RCA, which are important agronomic traits. Attempts are being made to breed for increased aerenchyma using interspecific introgression between teosintes (Zea nicaraguensis), which constitutively forms RCA, and maize (Zea mays subsp. mays) (Mano, Y. & Omori, F. Flooding tolerance in interspecific introgression lines containing chromosome segments from teosinte (Zea nicaraguensis) in maize (Zea mays subsp. mays). Ann. Bot. 112, 1125-1139 (2013)). Interestingly variation in aerenchyma formation reported in our current study occurred in field-grown maize plants grown in well-drained, fertile soil. Similar ranges of variation were found in greenhouse-grown plants, even though mean RCA formation was greater in field grown plants compared with greenhouse-grown plants (Burton, A. L. et al. QTL mapping and phenotypic variation of root anatomical traits in maize (Zea mays L.). Theor. Appl. Genet. 128, 93-106 (2015)). Despite substantial environmental variation in our current study, broad-sense heritability (H2) was high for the aerenchyma trait (Table 1). Our observations suggest that considerable variation for aerenchyma exists in non-stressed maize and breeding for aerenchyma traits can be carried out within Zea mays.

Evidence from biochemical studies and microarray analysis indicates that several genes related to the generation or scavenging of reactive oxygen species, cell signaling, cell wall modification, ethylene pathway, and proteolysis are differentially expressed during aerenchyma formation (Rajhi, I. et al. Identification of genes expressed in maize root cortical cells during lysigenous aerenchyma formation using laser microdissection and microarray analyses. New Phytol. 190, 351-368 (2011), Takahashi, H., Yamauchi, T., Rajhi, I., Nishizawa, N. K. & Nakazono, M. Transcript profiles in cortical cells of maize primary root during ethylene-induced lysigenous aerenchyma formation under aerobic conditions. Ann. Bot. 115, 879-894 (2015)).

Figures 2A, 2B, 2C, 2D, 2E, 2F:
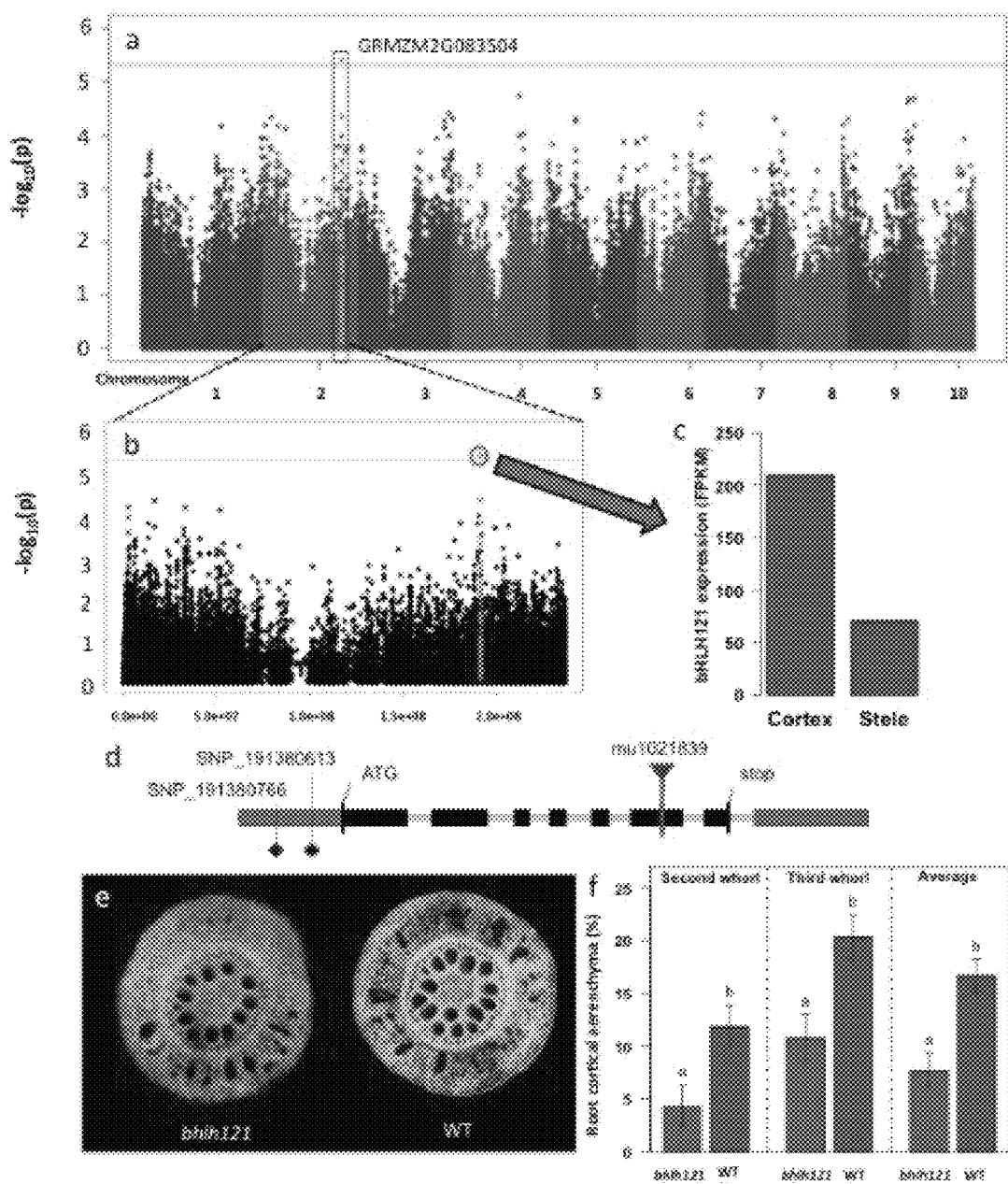
FIGS. 2A-2F depicts the workflow for the discovery and phenotypic validation of the mutant locus associated with root cortical aerenchyma in maize roots. (a) Manhattan plot of GWAS results for root cortical aerenchyma. The chromosome-wide significance threshold (horizontal line) was set using the simple M method ($-\log_{10}p=5.32$). Significant SNPs are located in gene model GRMZM2G083504 (bHLH121) encoding a bHLH transcription factor. All SNPs that lie within bHLH121 are indicated by the green dots. (b) Expansion of the Manhattan plot for chromosome 2. The most significant SNP associated with gene model GRMZM2G083504 (bHLH121) is located at position 191380613 bp on chromosome 2. (c) Relative expression of bHLH121 in the stele and cortex of a primary root from a 3 day-old maize seedling. (d) Schematic diagram for bHLH121 gene model: exons are represented by black boxes, and introns and the noncoding regions are represented by the gray lines and grey boxes, respectively. The blue triangle shows Mu transposon insertion, and the star symbols indicate the two significant SNPs identified by GWAS. (e) Root cross section of typical wildtype (WT) and bhlh121 (Uniform Mu insertion line). The root segments were collected at 8 cm from the base of the third whorl crown roots at anthesis. (f) Percentage of root cortical aerenchyma compared between wildtype and the bhlh121 mutant line of field grown plants at anthesis. The data shown are mean±SE of the mean from two field sites. Different letters represent significant differences compared within each group.

To identify novel regulatory genes that control root aerenchyma formation, GWAS for the root aerenchyma trait was performed with 436 inbred lines in the WiDiv population using a total of 438,222 RNA-seq based SNPs (Hansey, C. N., Johnson, J. M., Sekhon, R. S., Kaeppler, S. M. & Leon, N. De. Genetic diversity of a maize association population with restricted phenology. Crop Sci. 51, 704-715 (2011), Hirsch, C. N. et al. Insights into the maize pan-genome and pan-transcriptome. Plant Cell 26, 121-135 (2014)). Two SNP markers were significantly associated with RCA and lay within one gene model GRMZM2G083504 on chromosome 2 (FIGS. 2a and 2b). This gene encoded a bHLH transcription factor (ZmbHLH121). bHLH proteins belong to a superfamily of transcription factors that have been shown to be involved in diverse processes including programmed cell death (Niu, N. et al. EAT1 promotes tapetal cell death by regulating aspartic proteases during male reproductive development in rice. Nat. Commun. 4, 1445 (2013)). For example, the rice bHLH

TABLE 1

Anatomical traits, phenotypic variation, and broad-sense heritability (H2) values calculated on an entry-mean basis for the WiDiv over three field seasons.

| Trait | Unit | Minimum | Mean | Maximum | Range | $H^2$ |
| --- | --- | --- | --- | --- | --- | --- |
| Cortical cell size | $\mu m^2$ | 11 | 221 | 558 | 51x | 0.30 |
| Cortical cell number | count | 222 | 687.49 | 1,669.67 | 8x | 0.38 |
| Cortical cell file number | count | 5 | 8.89 | 12.67 | 3x | 0.43 |
| Living cortical area | $mm^2$ | 0.32 | 0.73 | 1.71 | 5x | 0.38 |
| Aerenchyma area | $mm^2$ | 0 | 0.18 | 0.64 | 64x | 0.50 |
| Root cortical aerenchyma | % | 0 | 15.4 | 41.01 | 41x | 0.59 |
| Root cross sectional area | $mm^2$ | 0.5 | 1.16 | 2.37 | 5x | 0.38 |
| Total cortical area | $mm^2$ | 0.41 | 0.93 | 1.92 | 5x | 0.37 |
| Total stele area | $mm^2$ | 0.09 | 0.25 | 0.51 | 5x | 0.56 |
| Median metaxylem vessel area | $\mu m^2$ | 2,778 | 6,148 | 13,696 | 5x | 0.61 |
| Total metaxylem vessel area | $mm^2$ | 0.02 | 0.06 | 0.14 | 7x | 0.55 |
| Metaxylem vessel number | count | 5.33 | 9.77 | 15 | 3x | 0.53 |

Earlier studies employing quantitative genetic analysis for constitutive aerenchyma formation have identified Quantitative Trait Loci (QTL) on chromosome 1, 5, and 8 in maize×Zea nicaraguensis mapping populations (Mano, Y. et al. QTL mapping of root aerenchyma formation in seedlings of a maize×rare teosinte 'Zea nicaraguensis' cross. Plant Soil 295, 103-113 (2007)). An additional QTL for aerenchyma area was identified on chromosome 8 in a maize recombinant inbred population (Burton, A. L. et al. QTL mapping and phenotypic variation of root anatomical traits in maize (Zea mays L.). Theor. Appl. Genet. 128, 93-106 (2015)). However, to date, only a flooding-induced gene, xet1, encoding a xyloglucan endo-trans-glycosylase has been associated with RCA formation in maize (Subbaiah, C. C. & Sachs, M. M. Molecular and cellular adaptations of maize to flooding ftress. Ann. Bot. 90, 119-127 (2003)).

transcription factor Eternal Tapetum 1 (EAT1) has been shown to be involved in late pollen development. EAT1 positively regulates programmed cell death in tapetal cells by promoting aspartic proteases triggering plant programmed cell death. Loss of function of EAT1 results in delayed tapetal PCD and aborted pollen development leading to complete male sterility (Niu, N. et al. EAT1 promotes tapetal cell death by regulating aspartic proteases during male reproductive development in rice. Nat. Commun. 4, 1445 (2013)). In maize roots, programmed cell death is a key process leading to RCA formation (Gunawardena, A. H. L. A. N. et al. Characterisation of programmed cell death during aerenchyma formation induced by ethylene or hypoxia in roots of maize (Zea mays L.). Planta 212, 205-214 (2001), Drew, M. C., He, C. J. & Morgan, P. W. Programmed cell death and aerenchyma formation in roots.

*Trends Plant Sci.* 5, 123-127 (2000)). Given the biological relevance of bHLH transcription factors, ZmbHLH121 was further characterized.

In order to genetically validate a role for ZmbHLH121 in aerenchyma formation, the inventors characterized a transposon-tagged mutant line harboring a Uniform Mu transposon insertion in exon 6 of the ZmbHLH121 gene (FIG. 2d). Plants homozygous for the mutant zmbhlh121 allele displayed a decrease in RCA in both second and third whorl crown roots by an average of 56% (FIGS. 2e and 2f). These results indicate that the bHLH121 gene functions as a positive regulator of RCA formation in maize roots.

The inventors next investigated ZmbHLH121 spatial and temporal expression. Analysis of the maize gene expression atlas (Sekhon, R. S. et al. Genome-wide atlas of transcription during maize development. *Plant J.* 66, 553-563 (2011), Stelpflug, S. C. et al. An expanded maize gene expression atlas based on RNA-sequencing and its use to explore root development. *Plant Genome* (2015). doi:10.3835) revealed that the ZmbHLH121 gene is expressed in root and shoot organs (FIG. 3). The root tissues included primary, seminal, crown and brace root classes. Consistent with a positive regulatory function during RCA formation, ZmbHLH121 transcript abundance was elevated in cortical parenchyma tissues of the primary root (FIG. 2c). Moreover, ZmbHLH121 was up-regulated in the root differentiation zone compared to the root apical meristem and elongation zones (FIG. 3), in agreement with the later onset of cortical aerenchyma formation.

In summary, despite their potential as target traits for plant breeding, little is known about the genes that regulate root anatomical traits in crops. This is primarily because of the practical difficulties in obtaining many thousands of root cross sections, imaging them and then quantifying root phenotypes. Here, the inventors report the Anatomics approach, a high throughput phenotyping pipeline for root anatomical traits, which the inventors have used to examine phenotypic variation for anatomical traits in maize. In our current study, the inventors demonstrated how a combination of Anatomics and GWAS of field-grown plants led to the identification of ZmbHLH121, a novel regulatory gene controlling root cortical aerenchyma formation. bHLH family members have previously been shown to be involved in programmed cell death (PCD) which is an important developmental process in aerenchyma formation (Niu, N. et al. EAT1 promotes tapetal cell death by regulating aspartic proteases during male reproductive development in rice. *Nat. Commun.* 4, 1445 (2013), Drew, M. C., He, C. J. & Morgan, P. W. Programmed cell death and aerenchyma formation in roots. *Trends Plant Sci.* 5, 123-127 (2000)). A transposon insertion in the bHLH gene exhibited decreased RCA formation, validating our GWAS results. This observation also indicated that ZmbHLH121 acts as a positive regulator of RCA formation, consistent with our expression analysis where its transcript was more abundant in older root cortical tissues where RCA forms. Our results demonstrate that Anatomics is an effective discovery platform for novel genes underlying variation for root anatomical traits. Moreover, it provides an exemplar for selecting crops based on their cell/tissue-scale (rather than architectural and/or physiological) properties.

Materials and Methods

Plant Materials and Growth Conditions

Four hundred and thirty-six maize lines of the Wisconsin diversity panel (WiDiv) were employed in this study. Experiments were conducted from January to April of 2011 and 2012 and from November to February of 2013 at the Ukulima Root Biology Center (URBC) in Alma, Limpopo province, ZA (24°33' 00.12 S, 28° 07'25.84 E, 1235 masl) using a randomized complete block design with two replications in each year. The soil at the experimental site was a Clovelly loamy sand (Typic Ustipsamment). Each maize line was planted in a single row plot consisting of 20 plants per plot. Row width was 75 cm, and distance within a row was 23 cm. In all trials, soil nutrient levels were adjusted to meet the requirements for maize production as determined by soil tests at the beginning of the growing seasons. The trials were irrigated using a center pivot system. Pest and disease control was implemented as needed.

Root Sampling

Roots were sampled 7 to 8 weeks after planting. Root excavation was carried out using 'shovelomics' (Trachsel, S., Kaeppler, S. M., Brown, K. M. & Lynch, J. P. Shovelomics: high throughput phenotyping of maize (*Zea mays* L.) root architecture in the field. *Plant Soil* 314, 75-87 (2011)). Three representative plants were selected for excavation in each plot. The selection was based on height, presence of bordering plants, and general appearance that represented individuals in the plot. Root crowns were collected by carefully removing a soil monolith containing the intact roots. The monolith was 30 cm in diameter by 15 cm deep centered on the stem. A large portion of the soil was removed from the roots by careful shaking. The remaining soil was removed by soaking the roots in diluted commercial detergent followed by vigorously rinsing at low pressure with water. A 4 cm root segment was collected 8 cm from the base of the second whorl crown roots. The samples were stored in 70% (v/v) ethanol at 4° C. until processing and analysis.

Laser Ablation and Image Capture

LAT was used to obtain cross-sectional images of all root samples. This LAT platform combined a nanosecond pulsed UV laser (Avia 355-7000; Coherent, Santa Clara, Calif.) focused into a beam using a galvanometer scanner (HurryScan 10; Scanlab, Puchheim, Germany) for surface ablation of the sample, a three-axis motorized stage (ATS100-100; Aerotech Inc, Pittsburgh, Pa.) to position and move the sample, and a camera (Canon EOS Rebel T3i; Canon USA Inc., Melville, N.Y.) and macro lens (65 mm MP-E 1-5× variable magnification; Canon USA Inc., Melville, N.Y.) for image capture. The laser beam, stage, and camera were operated remotely via computer. Winlase Professional software (Lanmark Controls Inc., Acton, Mass.) was used to set the dimensions and power of the laser beam. GalilTools software (Galil, Rocklin, Calif.) was used for stage control. EOS Utility software (Canon USA Inc., Melville, N.Y.) was used for image capture, with standard settings maintained for all samples, and the lens set at 5× magnification. The scale for all images at this magnification was 1173 pixels per mm.

Each root segment was secured on the stage perpendicular to the laser beam using a notched microscope slide, moved into the beam at 30 microns per second for 10 seconds while images were captured, and three cross-sectional images per root were saved for analysis.

Quantification of Root Anatomical Traits

Root anatomical traits were quantified using a semi-automated image analysis program RootScan (Burton, A. L., Williams, M., Lynch, J. P. & Brown, K. M. RootScan: Software for high-throughput analysis of root anatomical traits. *Plant Soil* 357, 189-203 (2012)). The analysis of images was performed in MatLab 7.6 2008a (The MathWorks Company, Natick, Mass., USA). RootScan separates different type of root tissues by using pixel thresholds. The following measurements were made via pixel-counting: root cross sectional area, aerenchyma area, total stele area, total xylem vessel area, and median individual metaxylem area. Pixel values were converted to mm or mm$^2$, based on micrometer calibration (1173 pixels/linear mm). Count data included number of cortical cells, cortical cell file number, and number of metaxylem vessels. Some of these primary measurements were used to calculate secondary measurements in RootScan: total cortical area (cross-sectional area–stele area), percent aerenchyma (total aerenchyma area/cross-sectional area), and living cortical area (total cortical area-aerenchyma area). In total 12 root anatomical traits were evaluated in this study.

Statistical Analysis

Statistical analyses were performed using R version 2.15.1 (R Core team. R: A language and environment for statistical computing. *R Foundation for Statistical Computing, Vienna, Austria* (2012). at R-project.org). Linear mixed-effect models were fit using the function lmer from the package lme4 (Bates, D., Maechler, M. & Bolker, B. lme4: Linear mixed-effects models using S4 classes. (2013). at CRAN.R-project.org/package=lme4). Variation within each trait and among years was assessed using two-way analysis of variance. Broad-sense heritability (H$^2$) on an entry mean basis was calculated for each trait according to Fehr (1987) (Fehr, W. R. Principle of cultivars development. Theory and Technique. (Macmillan Publishing, 1987)).

$$H^2 = \frac{\sigma^2(G)}{\frac{\sigma^2(E)}{ry} + \frac{\sigma^2(GY)}{r} + \sigma^2(G)}$$

where $\sigma^2(G)$ is the genotypic variance, $\sigma^2(GY)$ is the genotype by year variance, $\sigma^2(E)$ is the error variance, r is the number of replicates per year, and y is the number of years.

Genome-Wide Association Analysis

A Genome-Wide Association Study (GWAS) was performed with 436 lines of the WiDiv using a set of 438,222 RNA-seq based SNPs (Hansey, C. N., Johnson, J. M., Sekhon, R. S., Kaeppler, S. M. & Leon, N. De. Genetic diversity of a maize association population with restricted phenology. *Crop Sci.* 51, 704-715 (2011), Hirsch, C. N. et al. Insights into the maize pan-genome and pan-transcriptome. *Plant Cell* 26, 121-135 (2014)). Prior to the GWAS, data were power-transformed using the lambda identified by Box-cox transformations. GWAS was performed with the Genomic Association and Prediction Integrated Tool (GAPIT) package in R using a mixed linear model (MLM) written as follows (Lipka, A. E. et al. GAPIT: genome association and prediction integrated tool. *Bioinformatics* 28, 2397-2399 (2012))

$$y = X\beta + Wm + Qv + Zu + e$$

where y is a vector of phenotypic observations; β is a vector of unknown fixed effects other than the SNP under testing, m is a vector of fixed marker effect (e.g. SNP), v is a vector of subpopulation effects, u is a vector of unknown random effects, e is a vector of residual effects. Q is an incidence matrix of principal component scores (eigenvectors) of marker-allele frequencies. X, W and Z are incidence matrices of ones and zeros relating y to β, m and u, respectively. The covariance of u is equal to KVA, where K is the kinship matrix that was estimated with a random set of SNPs according to the VanRaden method and VA is the additive variance estimated with restricted maximum likelihood (REML). The kinship matrix estimation and the principal component (PC) analysis were performed with the GAPIT package. The optimum number of PCs/Covariates to include for each phenotype was determine by forward model selection using the Bayesian information criterion (BIC).

In this study, the inventors implemented the simpleM method (Gao, X., Starmer, J. & Martin, E. R. A multiple testing correction method for genetic association studies using correlated single nucleotide polymorphisms. *Geneic Epidemiol.* 32, 361-369 (2008)), which applies a Bonferroni correction to the effective number of independent tests, to determine the genome-wise and chromosome-wise significance thresholds.

Expression pattern of gene models associated with the significant SNPs and their adjacent genes were examined using a comprehensive atlas of global transcription profiles across developmental stages and plant organs database (Sekhon, R. S. et al. Genome-wide atlas of transcription during maize development. *Plant J.* 66, 553-563 (2011), Stelpflug, S. C. et al. An expanded maize gene expression atlas based on RNA-sequencing and its use to explore root development. *Plant Genome* (2015). doi:10.3835).

Mutant Lines

The zmbhlh121 mutant allele (mu1021839::Mu, stock ID: UFMu-01678) was obtained from the Maize Genetics Stock Center-Uniform Mu collection. Seeds from the Stock Center were grown at West Madison Agricultural Research Station during the summer of 2014 and genotyped for the transposon insertion. DNA was isolated by CTAB method and all primers were designed by Primer 3 based on B73 reference sequence. Plants carrying the mutant allele were identified by genotyping using an outward facing primer in the TIR of the Mutator transposon, TIRE (5'-AGAGAAGCCAACGC-CAWCGCCTCYATTTCGTC-3') (SEQ ID NO:2) and the ZmbHLH121 gene specific primer ZmbHLH121 R3 (5'-TTTCAGCTCGCAGTCGCAGTCGCAGG-3') (SEQ ID NO:3). The wild-type allele was identified by using the gene-specific primer set ZmbHLH121 F2 (5'-TCCA-GTCGCTGCAGCAGCAAGTTGAGG-3') (SEQ ID NO:4) and ZmbHLH121 R3. PCR conditions were 95° C. for 30 s, 63° C. for 30 s, 72° C. for 45 s, repeated for 30 cycles. The progeny of plants that tested homozygous positive for the insertion were used for phenotype analysis. Mutants and wildtype control plants (W22) were grown at West Madison Agricultural Research Station, Wis., USA (Latitude: 43°03'37"N; Longitude: 89°31'54"W) and at the Russell E. Larson Agricultural Research Center in, PA, USA (Latitude: 40°42'37"0.52N; Longitude: 77°57'07"0.54W)) during the summer of 2015. Root samples were collected at eight cm from the base of the second and the third whorl crown roots at anthesis. The samples were stored in 70% (v/v) ethanol at 4° C. until processing and analysis. Three images were captured per root, and analyzed with RootScan.

As can be appreciated, the results described in the above examples support the utility of the materials and methods described and claimed herein. Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific materials, methods, formulations, reaction/assay conditions, etc., herein illustrated and described, but embraces such modified forms thereof as come within the scope of the following claims.

LITERATURE CITED IN EXAMPLE 1

1. Hansey, C. N., Johnson, J. M., Sekhon, R. S., Kaeppler, S. M. & Leon, N. De. Genetic diversity of a maize association population with restricted phenology. *Crop Sci.* 51, 704-715 (2011).
2. Lynch, J. P. Root phenes that reduce the metabolic costs of soil exploration: opportunities for 21st century agriculture. Plant. Cell Environ. 1775-1784 (2014).
3. Grassini, P., Eskridge, K. M. & Cassman, K. G. Distinguishing between yield advances and yield plateaus in historical crop production trends. *Nat. Commun.* 4, 2918 (2013).
4. Sutton, M. A. et al. Too much of a good thing. *Nature* 472, 159-161 (2011).
5. Lynch, J. P. Roots of the second green revolution. *Aust. J. Bot.* 55, 493-512 (2007).
6. Postma, J. A. & Lynch, J. P. Root cortical aerenchyma enhances growth of *Zea mays* L. on soils with suboptimal availability of nitrogen, phosphorus and potassium. *Plant Physiol.* 156, 1190-1201 (2011).
7. Richards & Passioura. A breeding program to reduce the diameter of the major xylem vessel in the seminal roots of wheat and its effect on grain yield in rain-fed environments. *Aust. J. Agric. Res.* 40, 943-950 (1989).
8. Chimungu, J. G., Brown, K. M. & Lynch, J. P. Reduced root cortical cell file number improves drought tolerance in maize. *Plant Physiol.* 166, 1943-1955 (2014).
9. Chimungu, J. G., Brown, K. M. & Lynch, J. P. Large root cortical cell size improves drought tolerance in maize. *Plant Physiol.* 166, 2166-2178 (2014).
10. Saengwilai, P., Nord, E., Chimungu, J., Brown, K. & Lynch, J. Root cortical aerenchyma enhances nitrogen acquisition from low nitrogen soils in maize (*Zea mays* L.). *Plant Physiol.* 166, 726-735 (2014).
11. Chimungu, J. G. et al. Utility of root cortical aerenchyma under water limited conditions in tropical maize (*Zea mays* L.). *Field Crops Res* 171, 86-98 (2015).
12. Burton, A. L., Williams, M., Lynch, J. P. & Brown, K. M. RootScan: Software for high-throughput analysis of root anatomical traits. *Plant Soil* 357, 189-203 (2012).
13. Mano, Y. & Omori, F. Flooding tolerance in interspecific introgression lines containing chromosome segments from teosinte (*Zea nicaraguensis*) in maize (*Zea mays* subsp. *mays*). *Ann. Bot.* 112, 1125-1139 (2013).
14. Burton, A. L. et al. QTL mapping and phenotypic variation of root anatomical traits in maize (*Zea mays* L.). *Theor. Appl. Genet.* 128, 93-106 (2015).
15. Mano, Y. et al. QTL mapping of root aerenchyma formation in seedlings of a maizexrare teosinte '*Zea nicaraguensis*' cross. *Plant Soil* 295, 103-113 (2007).
16. Subbaiah, C. C. & Sachs, M. M. Molecular and cellular adaptations of maize to flooding ftress. *Ann. Bot.* 90, 119-127 (2003).
17. Rajhi, I. et al. Identification of genes expressed in maize root cortical cells during lysigenous aerenchyma formation using laser microdissection and microarray analyses. *New Phytol.* 190, 351-368 (2011).
18. Takahashi, H., Yamauchi, T., Rajhi, I., Nishizawa, N. K. & Nakazono, M. Transcript profiles in cortical cells of maize primary root during ethylene-induced lysigenous aerenchyma formation under aerobic conditions. *Ann. Bot.* 115, 879-894 (2015).
19. Hirsch, C. N. et al. Insights into the maize pan-genome and pan-transcriptome. *Plant Cell* 26, 121-135 (2014).
20. Niu, N. et al. EAT1 promotes tapetal cell death by regulating aspartic proteases during male reproductive development in rice. *Nat. Commun.* 4, 1445 (2013).
21. Gunawardena, A. H. L. A. N. et al. Characterisation of programmed cell death during aerenchyma formation induced by ethylene or hypoxia in roots of maize (*Zea mays* L.). *Planta* 212, 205-214 (2001).
22. Drew, M. C., He, C. J. & Morgan, P. W. Programmed cell death and aerenchyma formation in roots. *Trends Plant Sci.* 5, 123-127 (2000).
23. Sekhon, R. S. et al. Genome-wide atlas of transcription during maize development. *Planta.* 66, 553-563 (2011).
24. Stelpflug, S. C. et al. An expanded maize gene expression atlas based on RNA-sequencing and its use to explore root development. *Plant Genome* (2015). doi: 10.3835
25. Trachsel, S., Kaeppler, S. M., Brown, K. M. & Lynch, J. P. Shovelomics: high throughput phenotyping of maize (*Zea mays* L.) root architecture in the field. *Plant Soil* 314, 75-87 (2011).
26. R Core team. R: A language and environment for statistical computing. *R Foundation for Statistical Computing, Vienna, Austria* (2012). at <URL http://www.R-project.org/>
27. Bates, D., Maechler, M. & Bolker, B. lme4: Linear mixed-effects models using S4 classes. (2013). at <http://CRAN.R-project.org/package=lme4>
28. Fehr, W. R. Principle of cultivars development. Theory and Technique. (Macmillan Publishing, 1987).
29. Lipka, A. E. et al. GAPIT: genome association and prediction integrated tool. *Bioinformatics* 28, 2397-2399 (2012).
30. Gao, X., Starmer, J. & Martin, E. R. A multiple testing correction method for genetic association studies using correlated single nucleotide polymorphisms. *Geneic Epidemiol.* 32, 361-369 (2008).

We claim:

1. A recombinant maize plant tolerant of abiotic stress, comprising a non-natural mutation that increases the function of maize gene GRMZM2G083504, wherein the recombinant maize plant exhibits increased root cortical aerenchyma (RCA) and increased abiotic stress tolerance as compared to a maize plant lacking said mutation.

2. The maize plant of claim 1 wherein the increase in RCA is between 1% and 80%.

3. The maize plant of claim 1 wherein the non-natural mutation comprises an increase in the number of GRMZM2G083504 copies in the plant.

4. The maize plant of claim 1 wherein the non-natural mutation comprises a modification of sequences regulating GRMZM2G083504.

5. A method of increasing abiotic stress tolerance in maize, comprising introducing in maize a non-natural mutation that increases the function of maize gene GRMZM2G083504, wherein said maize exhibits increased abiotic stress tolerance as compared to maize lacking said mutation.

6. A method of increasing root cortical aerenchyma (RCA) in maize, comprising introducing in maize a non-natural mutation that increases the function of maize gene GRMZM2G083504, wherein said maize exhibits increased root cortical aerenchyma (RCA) as compared to maize lacking said mutation.

7. A method of identifying an abiotic stress tolerant maize plant, comprising: (a) assaying expression levels of a maize gene GRMZM2G083504 in maize plants; and (b) selecting a maize plant having an increased level of maize gene GRMZM2G083504 expression, wherein said selected maize plant exhibits increased abiotic stress tolerance as compared to a maize plant not having the increased level of maize gene GRMZM2G083504 expression.

8. A method for providing an abiotic stress tolerant maize plant variety, comprising: (a) assaying expression levels of maize gene GRMZM2G083504 in maize plants; (b) selecting a maize plant exhibiting increased levels of maize gene GRMZM2G083504 expression; and (c) breeding said selected maize plant exhibiting increased levels of maize gene GRMZM2G083504 to yield a maize plant variety providing increased tolerance to abiotic stress.

* * * * *

UNITED STATES PATENT AND TRADEMARK OFFICE
CERTIFICATE OF CORRECTION

| | |
|---|---|
| PATENT NO. | : 10,440,911 B2 |
| APPLICATION NO. | : 15/704502 |
| DATED | : October 15, 2019 |
| INVENTOR(S) | : Shawn Michael Kaeppler et al. |

Page 1 of 1

It is certified that error appears in the above-identified patent and that said Letters Patent is hereby corrected as shown below:

In the Specification

Column 20, Line 35, "TIRE" should be --TIR6--.

Signed and Sealed this
Tenth Day of December, 2019

Andrei Iancu
*Director of the United States Patent and Trademark Office*

SEQUENCE LISTING

```
<160> NUMBER OF SEQ ID NOS: 5

<210> SEQ ID NO 1
<211> LENGTH: 2570
<212> TYPE: DNA
<213> ORGANISM: Zea mays

<400> SEQUENCE: 1
gcagcaaagc aagctaaagg agagaaacct catatacttg cactttcgtc ataatcgtaa      60
gatcagaaaa aaaatgcaac aaacatgaca cggtatcgtt ccagtaccag ccaccagcgg     120
```

| | |
|---|---|
| tcttacatag gagtaataat cagtacagct tcagatgatg gcgcatgtaa tatttgcgcc | 180 |
| atatctacct agcacacgac ctactccaat ttttcacgag atgggtcgca cgatctctat | 240 |
| gggggcaag aatcgagtcg ccatgtgaca tacgtgcagc agtatcacgg aatgaatttc | 300 |
| agctcgcagt cgcagtcgca ggcctaaacg ctaatgatgg tcagcttagc agaggagagc | 360 |
| tctgcttgaa acacacagcc cacacacagg tcttggtacc accaccacct atgtacaaaa | 420 |
| ataccagccc ttgcagatca ccagggacgg gctagaactc agccttcgcc tgatcagctt | 480 |
| gcaactggcc tgcatcacat acatatacag caacacatgg ttgggttatc agtcaaataa | 540 |
| tggtaatctc ccgaatggtg cgcgcttcaa ttgatcgtcc atcactcaca taccatcaaa | 600 |
| ggtcgggtac taaaagccca tcctcctcct gcctttgctc gctaccggta gtaggggtag | 660 |
| gcaaagcatg ctgtaggcca tcctcccaca agtcccttttg ctgagaaata tgccagaact | 720 |
| gttataagat ccatattgac agccattaac tagctataca gattgctgat tcctcgggca | 780 |
| aacatttcta cctgcttttg aaaagcaaac tgtgggctgg ccgcgtgggg cagagccgtg | 840 |
| tctagcagca ggcttagaga gcactgatcc tccataccac taccgctacc gctaccaccc | 900 |
| gagccaaagc tgtggaaaag atccgcctgc tcgcagaatg gaaaagctgc gccggcgctt | 960 |
| tccagtggaa agaccgaact tgccgaaggg ccaccacatg gctgttggta catctgaatt | 1020 |
| aaccaggata aaatagcgtg tgtcaagggc ggatttgatg tgcaggtaca gagcatcgga | 1080 |
| gattgatgtg tgggtcaagc tcacgtcttt gtgcaggagt gtcgataggt tgctgaaatc | 1140 |
| aagctctggg ttcacagtgg cgagcttcat ggacaggaac tgaataaaag tagtgttaat | 1200 |
| aaacagcaaa agaaaaaaaa aacgattgga atctcgagct atgactgtgt tattatgtaa | 1260 |
| ccaaatgtaa gtggaaccct cgcctcacct caacttgctg ctgcagcgac tggacgtagt | 1320 |
| ttatgatctc atcgagcatg agtgccttgc cgaccaccta cagtagggaa tcccgtcaaa | 1380 |
| ttacaggcag caattgacac ttacacacga caattcactg tccaagaact ccatggccat | 1440 |
| accttgttgc atcctggcac taggtcctgt agaaatttca tcctctggct aatcttctct | 1500 |
| cttctaacct atcaagacac aaataacaaa agtgtggttg tgaattcaaa cccgaagcac | 1560 |
| aaaatttcca ttttgcgatt tagcccaaac ggtaggtaga aatggaattg cagtgtctta | 1620 |
| ccctctctgc aaggctgtgg ctgtcagtcg cctgccccg ccgcgcccgg acatggacgt | 1680 |
| agtctttggg cggttcgact gccggcttcg agctcttccc cttgcccttc ttctgcgctt | 1740 |
| tgacttcaac caaggcgtcg ctcgccgccg cctcctcctc ctcttccttc ggcttcaccg | 1800 |
| gactgtcgct ggcacccact actctgcacc tcttcccgtc cggacccttg gcctccgcaa | 1860 |
| cctgcaaacc aatatcgaga atggcggcac cggcacgtca agaaccagca agctaaattc | 1920 |
| aaagcacagt ccactgcgca cagtcgtttc gtttccgcac cttgctcaag caggcctcct | 1980 |
| tgccaccggc ggaccccgtg ggcggcgcct tgcgtttcct ggcattgccg tagtccctag | 2040 |
| cgcgcgccca cgctgggtcg gacaccgacg acccctccgg agacccgccg ccacaccctg | 2100 |
| cctccgcggg caccccgaag aggccccgc cgccgccgcc gcgtagcgtg tcgaggaacc | 2160 |
| cggcgtccag cgcggcgaag ctgagtgcag gggcggatga gcccatgagc aggctggcaa | 2220 |
| tgtagtcgct gtccattgaa acaaacaaag gcgctgccgc aggaattgcg caggaagcaa | 2280 |
| agggagggtg aggaagtctt gggtcgtctc tcgtctactg cgagctcgag tctgcaatgg | 2340 |
| atttggggga aagcgaagcg accgaggccg cggaaccggt aggtggggga ttgctttata | 2400 |
| gagcggttgt tgccgctgcg gttgggttgt gggccgcgcg ccgcatccgt cgcgtagctc | 2460 |

```
ggcgcggtgg gatgcttgcg gcggtgggtt accaccgggt tatactgcgg cggcgctcgc   2520
gcaggagagg ggagaaaagg cggtcaaaac gggacggagc gggcggaggt             2570

<210> SEQ ID NO 2
<211> LENGTH: 32
<212> TYPE: DNA
<213> ORGANISM: Artificial Sequence
<220> FEATURE:
<223> OTHER INFORMATION: synthetic

<400> SEQUENCE: 2
agagaagcca acgccawcgc ctcyatttcg tc                                  32

<210> SEQ ID NO 3
<211> LENGTH: 26
<212> TYPE: DNA
<213> ORGANISM: Artificial Sequence
<220> FEATURE:
<223> OTHER INFORMATION: synthetic

<400> SEQUENCE: 3
tttcagctcg cagtcgcagt cgcagg                                         26

<210> SEQ ID NO 4
<211> LENGTH: 27
<212> TYPE: DNA
<213> ORGANISM: Artificial Sequence
<220> FEATURE:
<223> OTHER INFORMATION: synthetic

<400> SEQUENCE: 4
tccagtcgct gcagcagcaa gttgagg                                        27

<210> SEQ ID NO 5
<211> LENGTH: 12570
<212> TYPE: DNA
<213> ORGANISM: Zea mays

<400> SEQUENCE: 5
gaatgctgat tgctgtgttg cagctcttcc tgctgaatta gttgctcatc tagcaagggg    60
ggttgagggt cttgctgagc gggctgctca ttcacaatcc actgatccca ctctccctgc   120
cccaagtcgt cctgctgagc cggcaacact ccaccctcag gctccggagg aaagttaagg   180
tcgagcccag ccggggcaa aggttggccc agcccgaaga aggccagggg gagctgatga    240
ccatcctcag gtggcggagg gatggggtcc tcgtcctgag cctgaccgcc aagcataagc   300
tgctggataa tttcacattg taccgtccag gaatcccag caaaaccctc agcctccgaa    360
aaaacaataa attgaggaac ctcctcaagc gaagtgaccc gaacacggag cagggttcta   420
gagatattgc ttcggtcctc ctcccacaga atcagcctcc cgaatgcccc aatggcggcc   480
tgcagatact ccgaagaacg ataatccaag ggaaagccca gaagcataag ccaacattca   540
tggttgaaga gaagggcacg gtggttccag gcatcattgt gacggaccgc ggtgaatgta   600
gcgtccaaat actgctgggg accaagaaga accaagttat cccgctccag cacactacgg   660
aattgcacca acacttgtcc caaatgtgag cgctgaatgg cacggacacc aaccctctga   720
tgctccacaa ggtattccct gaccacatcc ctaaccgcag ggaacaagac ctcgtgctcc   780
ggtaaaggat ggatatttat aatcgcccag tcctcatgaa atggcggcaa acgctgcgaa   840
actgacctga ccataatccc acgatgttgg accaccgcgg cgctgaatcc tggagggagg   900
aacggccccg ggtccacacg ccggtacgcc attgacagat tctcagacga tcgccggaga   960
```

```
gcaaagggtg gagaagcagg ttggggtttt gttgaagtga cacccaacgc gagctccaag    1020
gacgtctctg gcgcctgttc gggttttttt aataatgaaa ccgctttggc gaattcaccg    1080
aaggaggcaa atgaaggtgg agtcccaccc gtcagagacc tggaggatga gcggaaccag    1140
gacccgaagt ccaagggacg gagtgaccct tccaaagggc agatactttc gaaggaaggg    1200
aacgaggaga gagggaaacc aaattctgat tttttacgtt tgcagaacaa ttccaaatgc    1260
cccctggctt tacaaaaaag gcagaacaag gctgaagtag ccgagcccga caaatccgtc    1320
cttccaggcc caagcacagg cctgagggc ccgttacgca gaatgggccg ccactgcaac     1380
ctacgaggcc aatgtcgccc aacagaagaa tttgagatcg actttgaatt tgaaagggag    1440
caatcatcac agccccgaca accgcgccca ttcctgcacc cgttaggcct gggagaacac    1500
gccgcagggg cagactcacg atgaagatca cgcgacgagg ccccgaggt cgaagagttg     1560 gcaggagacc tcggaccccg agctccgaag gggaaaccca atctattgaa aacagaagtc    1620
ctcggagcaa tcaattttcc agctgaacag gaagaacgac gaagtcgacg aactggaaca    1680
gcatttgcac cagtcaaagg cgggcgccta accacatcag cgaatgagat ttttttcctg    1740
cccgagacaa accaccagtt ggcgttctcc tcctgaagaa atagcttgag ctcatagttc    1800
caatttggtc cacccgagtt ccacaagttg aagaaagctt tgaattcaga acgagcgatg    1860
catctggagt tgtagatgtg gaacccaaca tccctggagg aaaccgagaa acggaaaacc    1920
cgatcggcaa gcgggaggac catgaatccc ctggcagaac caccaaaagc agcttgaagg    1980
atgtgaccaa tcgagacagg atcaagcctg aagatgcatc ttccaaacga dcaacaagc    2040 cagaaagccg atggggagcg cgggcttccg gggcaaacag gagaggaaaa tcggcgccaa    2100
acatcagcct caaaaagcac ccccggccga aagtccagac gagacaaatc catcccccag    2160
cacgaagaag accaagcgag gagaggggga gagaagcgag aaccacgggt gcgaagtcga    2220
cgaagaagag ggggaccaag ctcagaacca actcacagga ggaagccgcg tgcgcgcggc    2280
cgcccgccga gcgcccagtt ggtcaccgcc atctccgcca ttggcagctc catctttcca    2340
tcaacggaga atgaggagg ggaagagcgg cgtcgcaacg ctgcggcgga aaccggccta     2400
cacaccgagg agagccggcg gcagcggggc tggggagaag cgagaaccac gggtgctcct    2460
tgtcttcagt ttggttgtat gttattatac tatctcatgt tttatgaccg gtggagccat    2520
ctgtgtctat gatttgtaga ctcggtggca tactagcgag acccacaaat cataatggca    2580
aaattgccaa tgtctggaca tccgaccctg cccaaacaga cagttttgct cgcagctagg    2640
aagccctact acagctgaac acgtcgatgt caccgaatag gactgatgaa gacagatgtt    2700
aaatgggaaa cgggctgact agtttatgcg agtagaggtt tgctagtgaa tgtatcccac    2760
aagcgtgagg aacacggggt atatcaacca gcttgacaaa cgacaacaac tgcaacagtg    2820
aagtaattat gtcatcccac gggtatcttg tttatgtttc agatgctaga gttcattta     2880 attttgtctt aggagatcac acttttttct agtttaggct aaatttacta tttaaatcgt    2940
ttcatcatta atttttttca tcaggcctat tttgacactg cgttttattt aaataaaatt    3000
ttactgccct ttgctatgaa gagtgtcatt ctggctgttt taagtcggct aatttcaaat    3060
taaattaaac ttataaaaaa cctatattat accggcattt atactaccaa ataaatgctt    3120
tctggctgtt ttaagtcggc taatttcaaa ttagattaaa cttataaaaa acatatatta    3180
taccggtatt tataatacca aataaaatgc tattagattc atcgttaaat acgattttgt    3240
tatattggta gcgttcgatc cgcgcgttgc agttgcaggg tgtgaacctt cgctggaaca    3300
```

```
cccccagttaa cattattgaa tatacctcgc taataaaaat atcgaaatga tctaccatag    3360
ctgaaacatt aaattcatag tgttgtctaa gaacactatc aaattaagca tccaggtgca    3420
tgcacgcatc atcgtttact tcaagaaaac catctgactg ccgttggtcg acattggact    3480
tttattgttt ttttttttctt acagactgcc acctaataaa aaacctcctt ttttttcttt    3540
tcttttcttc ccttgagtga ctgattgaag aaggaaactg gccgaataaa caacgagctc    3600
tcgttaggtc gtgaggagat gcatgcaaag gttagttgcc cccgaggaga tgcttatgca    3660
agttccagag tactctttgt ttgctgcaag ttgttggtgt tggctttgtt ttttttcctt    3720 tttcgttttcc gttccgtttg ctggtagtat tgtgtgcgtg tccgagtctt ggaggcatca    3780
aggcaagccc gttcttgcaa gaaagggcat cgtcgctgtg ttttttttc ccctcccaag    3840 tcttggaggc actgtttgtt ggcttggcca gtactactag cgcactcacg ttgcgtacga    3900
tccctctcgt gaggtgtgcg gctttgagcc gtcagttttc cacggccagc cccagcccca    3960
ctcctcgccg ccgagacgga cggaaactgc aaatcaaatg tgtgtgtgta ggaccgggac    4020
cgagcacgac gacacggaac ctacttgcac cagcaaccag cgctgaatac gccgtacgtg    4080 ttctttttaag atacgcgtag aagaaaatca tgcacgagaa tgaatggaaa tagagaggga    4140 gggggggcaca cagcacggcc cggcctgatc ctgatgccga cagtacaagg cttacggtgt    4200
agtagtagtg tacgtgtacc cttgcattgg tatactagtg cactgataca tggaaaatat    4260
attaatctca aatgttttca ctaatcctac acgaagccaa gccacctacc ggtctctgaa    4320
tcagaacacc cctctctgct agacaacgca gcgatagaga tgggggggaaa ctaactcctg    4380 cctgtgctgt gcgtgcgtgc ttgcgttgcg tctgcatgca tccggatatg cattgcagtt    4440
gcaggcggcg tttcctttcg caggcccggg cgttcgattg cctcttctgg attgaagcgt    4500
gcaagagcca tgaccgtcgt tgcggcgtgg atggatcacg gatgggagga gcgcagcagc    4560
ggacggacgg agtaccaaga aaaagagat ccagccggaa gcccagggaa aagcgacgga    4620
taacctaccg aaattgggga agacaacgac ggcttgtttc tacgtaaaag acggctacag    4680
gcaacaccca tttacgacga cgacgacctg acttgcacaa gcagatgagc tgtgttgcct    4740
acccgtggtt taaaactgtc aggttggtct tgctcgtttc tggtttctac cagcaatttc    4800
agaccagtct ttatattttt ttttcttgca aaaactacca ggacttacta tatatgtatg    4860
tctcatagcg tgaaccgtga gcgggtttca tcggtctgtg ggttcaagaa cacttcacta    4920
tatatagtct gtaaatgatg agcccatgcc acactcagtt gcagcaaaac taataaaaaa    4980
aacgatggcg cagaacattt gcagcaaagc aagctaaagg agagaaacct catatacttg    5040
cactttcgtc ataatcgtaa gatcagaaaa aaaatgcaac aaacatgaca cggtatcgtt    5100
ccagtaccag ccaccagcgg tcttacatag gagtaataat cagtcacgct tcagatgatg    5160
gcgcatgtaa tatttgcgcc atatctacct agcacacgac ctactccaat ttttcacgag    5220
atgggtcgca cgatctctat ggggggcaag aatcgagtcg ccatgtgaca tacgtgcagc    5280
agtatcacgg aatgaatttc agctcgcagt cgcagtcgca ggcctaaacg ctaatgatgg    5340
tcagcttagc agaggagagc tctgcttgaa acacacagcc cacacacagg tcttggtacc    5400
accaccacct atgtacaaaa ataccagccc ttgcagatca ccaggacgg gctagaactc    5460 agccttcgcc tgatcagctt gcaactggcc tgcatcacat acatatacag caacacatgg    5520
ttgggttatc agtcaaataa tggtaatctc ccgaatggtg cgcgcttcaa ttgatcgtcc    5580
atcactcaca taccatcaaa ggtcgggtac taaaagccca cctcctcct gcctttgctc    5640 gctaccggta gtaggggtag gcaaagcatg ctgtaggcca tcctcccaca agtcccttg    5700
```

```
ctgagaaata tgccagaact gttataagat ccatattgac agccattaac tagctataca    5760
gattgctgat tcctcgggca aacatttcta cctgcttttg aaaagcaaac tgtgggctgg    5820
ccgcgtgggg cagagccgtg tctagcagca ggcttagaga gcactgatcc tccataccac    5880
taccgctacc gctaccaccc gagccaaagc tgtggaaaag atccgcctgc tcgcagaatg    5940
gaaaagctgc gccggcgctt ccagtggaa  agaccgaact tgccgaaggg ccaccacatg    6000
gctgttggta catctgaatt aaccaggata aaatagcgtg tgtcaaggc  ggatttgatg    6060 tgcaggtaca gagcatcgga gattgatgtg tgggtcaagc tcacgtcttt gtgcaggagt    6120
gtcgataggt tgctgaaatc aagctctggg ttcacagtgg cgagcttcat ggacaggaac    6180
tgaataaaag tagtgttaat aaacagcaaa agaaaaaaaa aacgattgga atctcgagct    6240
atgactgtgt tattatgtaa ccaaatgtaa gtggaaccct cgcctcacct caacttgctg    6300
ctgcagcgac tggacgtagt ttatgatctc atcgagcatg agtgccttgc cgaccaccta    6360
cagtagggaa tcccgtcaaa ttacaggcag caattgacac ttacacacga caattcactg    6420
tccaagaact ccatggccat accttgttgc atcctggcac taggtcctgt agaaatttca    6480
tcctctggct aatcttctct cttctaacct atcaagacac aaataacaaa agtgtggttg    6540
tgaattcaaa cccgaagcac aaaatttcca ttttgcgatt tagcccaaac ggtaggtaga    6600
aatggaattg cagtgtctta ccctctctgc aaggctgtgg ctgtcagtcg cctgcccccg    6660
ccgcgcccgg acatggacgt agtctttggg cggttcgact gccggcttcg agctcttccc    6720
cttgcccttc ttctgcgctt tgacttcaac caaggcgtcg ctcgccgccg cctcctcctc    6780
ctcttccttc ggcttcaccg gactgtcgct ggcacccact actctgcacc tcttcccgtc    6840
cggacccttg gcctccgcaa cctgcaaacc aatatcgaga atggcggcac cggcacgtca    6900
agaaccagca agctaaattc aaagcacagt ccactgcgca cagtcgtttc gtttccgcac    6960
cttgctcaag caggcctcct tgccaccggc ggacccgtg  ggcggcgcct tgcgtttcct    7020
ggcattgccg tagtccctag cgcgcgccca cgctgggtcg acaccgacg  acccctccgg    7080 agacccgccg ccacaccctg cctccgcggg caccccgaag aggcccccgc cgccgccgcc    7140
gcgtagcgtg tcgaggaacc cggcgtccag cgcggcgaag ctgagtgcag gggcggatga    7200
gcccatgagc aggctggcaa tgtagtcgct gtccattgaa acaaacaaag gcgctgccgc    7260
aggaattgcg caggaagcaa agggagggtg aggaagtctt gggtcgtctc tcgtctactg    7320
cgagctcgag tctgcaatgg atttgggga  aagcgaagcg accgaggccg cggaaccggt    7380 aggtgggga  ttgctttata gagcggttgt tgccgctgcg gttgggttgt gggccgcgcg    7440
ccgcatccgt cgcgtagctc ggcgcggtgg gatgcttgcg gcggtgggtt accaccgggt    7500
tatactgcgg cggcgctcgc gcaggagagg ggagaaaagg cggtcaaaac gggacggagc    7560
gggcggaggt gtaaccgtgt agccaccgcg ctccgccggc aggccgagca aatgacggtc    7620
tctggcagct caccattgag gggcagtgct ccgggattta tggcttggga gaagacgtt     7680 tctgtcccct ctgttaacgc atcagggaag gtgctctccg gcgtgttgac agcctacact    7740
cgaccgtgaa agaattcata aaatatgccg tcttctaggt tgagtagttt gcggtgcgga    7800
tccaattaca taaataaata tataagaaaa atactatgaa agatagatct atgggcacga    7860
ggcaaggaca caaacgtaag actagaaaga aggcctatca cgagaataat tttagaaaga    7920
taaacataat aaagatatta tcagattagg agatatgatc tgaaaccaaa tagatatata    7980
aagatccata taggtaaaag aaaacaccat aaaaacaaag tttgactcct tgttagatcg    8040
```

-continued

```
tgatagactc gattatgtgt cttatcatac aatccaccta gatacacttt tgcgaaccat    8100
tgtatttcct tggactatat aaaagaagga ccgagggtgc cccacgaaga cagaagagat    8160
cattagataa gaatatgaat accggcacaa aacgggacgt agggcattat ctaatctcaa    8220
aagtataaac ttgtataaat cttagtgtct tttgtgcctt tagctttaga tttagctttt    8280
gattacgtga cctaccccat aaaatcacta tcgaatcaga ttttatagtt ggtgcgctag    8340
gtaggggtag ccacactaat caacaaagag ttgatggcaa ccatatgttt cacattagaa    8400
ggagaaatca tcttcaacac ccagagatct atcgatggct tgctctagtg gctttggcat    8460
catatgacca aaatcccgag gatacaatat tcatcttggc aaatctaggt caatttgata    8520
tcatgatatc tactcgaact cgaattggac ttcaatcatg gttcgaactt gtacatgagt    8580
ctaagttgga ctatgactcc aaccctaact tggattcggg cccagactcg aacctataga    8640
atccatttaa agattgcttc gagatcatgg ttgcttcgac gataagattg cttcgaatgg    8700
ttcgcgacct tagcatggac gatccgctcc tcgcacaacg gtctaatttg atagcccgac    8760
ggctatgact aataatctaa cggttatgaa tgacatatca acgactctct atccttggtg    8820
atttgacgtg gacggtctat ccttcggact gagcaaaaat accactagcg agcaatctgt    8880
gaattatggt gggatggtcc acacaaggac ccaaacaata cgtagcttag gctagacggt    8940
ccatagttca aatttatgaa accacaagtt catgtgtgtc ttctgatcat agtactccgg    9000
acggtctagc attagcgtcg gatgatccat gcttggcaat tttagaactt gagttttgt    9060
atatttgtcc atcttcaaag tatcttctcc aagtggatct ttgggtgttc ctatgattta    9120
gacaaccata tctagagact ttccaactag tccaagtcac agaatttggt cattttaatt    9180
catctaactc atagcctgat tcttgctcaa tcttagctcc aaaagagtga atctttgaat    9240
ctgagcattc aacctccct agatagatta aatagtttct atgggtgtta agaattcatc    9300
caaagtgtag aactaatgta agttcttctt ttccaaatac ttggcaaact tggtagtcca    9360
aatggttgtg atggtcatca agcaccaaaa caagtctaga aatggattaa gccccatttc    9420
acttccactc catctctgag ataatcacaa gaagtatatt gaaccaaggc tagggcacta    9480
agaagccact actagaggtt agtcaacatc tccttgtatt cacatctatg taacaaggtc    9540
ctcctcataa tgtcgttcaa gagatgaatc gctggtgtaa gctcactagg ttgtatctgg    9600
agcagtctta gaatggtggc ctaaagcagg ctactacgtg gaatgtccct aggagctctc    9660
caccttgagg gcatctaggt ggatccatag tatcatagca tgggttgtga agatgtgtgg    9720
ttgactctat aaacccaact ctcgcttttgg tagcattagc atatagtcta tgtggcttgc    9780
ctctaaaggc aaactaaaat tactcatagt caaggtggat ctaaagtgag gcatagaact    9840
ctctgactca ggcctcaact tataagccaa tcatcccaaa caatttgtca gtcttggtag    9900
ataagtgagg tagggatgaa tctagtatcc tcagcaacaa cgatgtcctc taaggaacaa    9960
actcgatgag gtatgagggg tgatccaatg tgagtcatgg ttgagtagaa gtcctcctgc   10020
agcaagtcta taaattgtct gatgctctag ggtcccctac tgctagaaac cactactcta   10080
ctggcacaaa gcggagctcc tatactcatg gtccttaggt caaggtaaat aactagtgga   10140
tgtgagagca cctagagggg ggtgaatagg tgatcctgtg aaacttgaaa acttaatgcc   10200
acaaaacttg gttaggcgtt agcacaataa tgccaagtgg ctagagagga gtctcaacaa   10260
aacacaataa ccacaagaga tcaatcacag agatggcaca gtggtttatc ccgtggttcg   10320
gccaagacca acgcttgcct actccacgtt gtggcgtccc aacggacgag gattgcaatc   10380
aaccccctctc aagcggtcca aagacatact tgaataccat ggtgtttgct tttctttttct   10440
```

```
atatcccgtt cgtgaggaat ctccacaact tggagtctct cgcccttaca aagatgttca   10500
caaagaagca cggagtaagg tagggattag caactcacac aagacacaaa gatcacggca   10560
aatacgcaca cacaagaccc agacttaagc tcaagagact agcacactag aacggagctc   10620
aaatcactag aatgtcgaac aagtgcgcaa gaatggagtg tgagtgatca agattgctca   10680
aggaatgctt ggtgtactcc tccatgtgcc tagaggtccc ttttatagcc ccaaggcagc   10740
taggagccgt tgagagcaat ccgggaaggc aattcttgcc ttctgtcgcc tggtgcaccg   10800
aacagtccgg tgcaccaccg gacactgtcc ggtgcggatt tccttcctta tttggcgaag   10860
ccgaccgttg gcagccttgg agccgttggc gcaccggaca ctgtccggtg cacaccggac   10920
agtccggtgc cccctcccga ccgttggctc ggccacgtgt ctcgcgcgga tcgcgcgacc   10980
gaccgttggc ccgccgacc gttggctcac cggacagtcc ggtgaattat agtcgtatgt   11040
tggggacttg ttctcaaatg ctatgagtta agaacaaggc aacacagaaa atgttaaatg   11100
gtaaagtcct tcgtccttcg aagcattatt tcccttagga tataatgatt ttcgacgaa    11160 ggttatgaag ggcgcacctt cataaacaca acatacgatg atgaagaatg aaccatatga   11220
aatatcaaga ataacataaa caattatatg ttattatcaa cttatttttg cattattatt   11280
atgaagaaat agaaatgaca tcaaattaca actgtacctt cggcttggaa ggagatgaaa   11340
atacaagtgt gacgcaaaag caaatgccaa gtcagcgtaa acagtacggg ggtactgttc   11400
acctatttat aggcacggga cacagcccat ataaaattac attcatgccc tttacatttg   11460
gtagtaattc tatagtaatc caccgaggtc tgaatagcct tttcatcttt aagtcggttt   11520 cttttctgc taccacgccg aagctttccc gctcacatct tcggcgttgt atcaaccttc    11580
gtattacttt gggcttctcc tactgtgata tcgactcgag tccgaagata cctattcaca   11640
cattatactc cagaaacact gttaaatcct gtttttgagg accttcggaa gccgaaggcc   11700
cccaacagta gcccctcgca atataaattt gttaaaataa taaatttaga ttgcgacatg   11760
tacgaagact ttaagcctaa ggtccgaaaa aacaccttcc ttttgctaga atagcaacat   11820
tcactgacaa gcggggtctt tcaattttta acgcactggg cgtataaata agagcatacc   11880
gcgagctcat ttggcacgct ctcttgccat ctgctctcgc tcactcaatt tttagctctt   11940
gcgcaccgag atttgcttag cttttttaagt ttttaagctt cggcgctgaa acagttttt    12000 tagtgtttcc gaagatgtct gaagataaga aggctgctct cgagatgaag ctgagtctct   12060
ctgaagagaa gaacctgggg tttcttatag caatgtcgaa gaccaacaca gaaaaaatca   12120
ccaaagagat tttagaaggt ttgtctgaag atactgatga cagcgacaat tatgatgtag   12180
atagtggtgg tgaagactcc gaagatcgcc cctggcgacc aagccattca gttttttagca   12240 aatcaggtat caaagaaaat catcttgtca acatgagggg aagatacttc cgggatttat   12300
ccattgtgag ggtcgacgaa ggagagaaga cttgcccgac ctctgaggaa aatgaagtcg   12360
tagtgttccg aagctttttg aaagctggac tacgatttcc tttgagcagc tttgtcgtag   12420
aagtgctgaa aatgtttgaa gtctatcttc atcaacttac ccccgaagca attataaggc   12480
tgaatatctt cgtgtgggcc gtgagaagcc aaggtctgga acctgatgcg aaaagtttct   12540
gcaacataca cgaattatca tacgagacaa                                     12570
```